United States Patent [19]
Adams et al.

[11] Patent Number: 5,840,835
[45] Date of Patent: Nov. 24, 1998

[54] INHIBITORS OF PEPTIDE BINDING TO MHC CLASS II PROTEINS

[75] Inventors: Alan D. Adams, Cranford; A. Brian Jones, Scotch Plains, both of N.J.

[73] Assignee: Merck & Co., Inc., Rahway, N.J.

[21] Appl. No.: 738,520

[22] Filed: Oct. 28, 1996

Related U.S. Application Data

[60] Provisional application No. 60/005,994, Oct. 30, 1995.
[51] Int. Cl.$^6$ .......................... A61K 38/00; A61K 38/04; C07K 5/00
[52] U.S. Cl. .......................... 530/323; 530/330; 530/331; 514/18; 514/19; 424/278.1; 424/810
[58] Field of Search .......................... 514/18, 19; 530/323, 530/330, 331; 424/278.1, 810

[56] References Cited

FOREIGN PATENT DOCUMENTS

| 0 532 466 | 3/1992 | European Pat. Off. . |
|---|---|---|
| WO88/03022 | 5/1988 | WIPO . |
| WO 96/01646 | 1/1996 | WIPO . |
| WO 96/20215 | 7/1996 | WIPO . |
| WO 96/30035 | 10/1996 | WIPO . |

OTHER PUBLICATIONS

Basak et al., Int. J. Peptide Protein Res., vol. 46 (1995), pp. 228–237, "Peptidyl substrates containing unnatural amino acid at the P'1 position are potent inhibitors of prohormone convertases".
Kroemer et al., J. Med. Chem., vol. 38 (1995), pp. 4917–4928, "3d–Quantitative structure–activity relationships of human immunodeficiency virus type–1 proteinase . . . ".
Scholz et al., J. Med. Chem., vol. 37 (1994), pp. 3079–3089, "Inhibitors of HIV–1 proteinase containing 2–heterosubstituted 4–amino–3–hydroxy–5–phenylpentanoic acid . . . ".
Chapman et al., J. Med. Chem., vol. 36 (1993), pp. 4293–4301, "Inhibition of matrix metalloproteinases by N–carboxyalkyl peptides".
Urban et al., FEBS, vol. 298, No. 1 (1992), pp. 9–13, "Reduced–bond tight–binding inhibitors of HIV–1 protease".
Hanson et al., Biorganic & Medicinal Chemistry Letters, vol. 6, No. 16 (1996), pp. 1931–1936, Design of MHC Class II (DR4) ligands using conformationally restricted imino acids at p3 and p5.
Sette et al., J. of Immunol., vol. 151 (1993), pp. 3163–3170, "HLA DR4w4–Binding motifs illustrate the biochemical basis of degeneracy and specificity in peptide–DR interactions".
Rudensky et al., Nature, vol. 359 (1992), pp. 429–431, "Truncation variants of peptides isolated from MHC Class II molecules suggest sequence motifs".
Chicz et al., Nature, vol. 358 (1992), pp. 764–768, "Predominant naturally processed peptides bound to HLA–DR1 are derived from MHC–related molecules and are heterogeneous in size".
Hammer et al., Cell, vol. 74 (1993), pp. 197–203, "Promiscuous and allele–specific anchors in HLA–DR–binding peptides".
Germain et al., Annu. Rev. Immunol., vol. 11 (1993), pp. 403–450, "The biochemistry and cell biology of antigen processing and presentation".
Jorgensen et al., Annu. Rev. Immunol., vol. 10 (1992), pp. 835–873, "Molecular components of T–cell recognition".
Stern et al., Nature, vol. 368 (1994), pp. 215–221, "Crystal structure of the human class II MHC protein HLA–DR1 complexed with an influenza virus peptide".
Hurtenbach et al., J. Exp. Med., vol. 177 (1993), pp. 1499–1504, "Prevention of autoimmune diabetes in non–obese diabetic mice by treatment with a Class II major histocompatibility complex–blocking peptide".
Guery et al., J. Exp. Med., vol. 177 (1993), pp. 1461–1468, "Selective immunosuppression by administration of major histocompatibility complex Class II–binding peptides".
Wauben et al., J. of Immunol., vol. 152 (1994), pp. 4211–4220, "Inhibition of experimental autoimmune encephalomyelitis by MHC Class II binding competitor peptides depends on the relative MHC binding affinity of the disease–inducing peptide".
Gautam et al., J. of Immunol., vol. 148 (1992), pp. 3049–3054, "Inhibition of experimental autoimmune encephalomyelitis by a nonimmunogenic non–self peptide that binds to I–Au1".
Skinner et al., Annals of the Rheumatic Diseases, vol. 53 (1994), pp. 171–177, "Lymphocyte responses to DR 1/4 restricted peptides in rheumatoid arthritis".
Hanson et al., Biorganic & Medicinal Chem. Lett., vol. 6, pp. 1931–1936 (1996), "Design of MHC Class II (DR4) ligands using conformationally restricted imino acids at p3 and p5".
Hammer et al., Proc. Nat'l Acad. Sci. USA, vol. 91, pp. 4456–4460 (1994), "High–affinity binding of short peptides to major histocompatibility complex class II molecules by anchor combinations".

(List continued on next page.)

Primary Examiner—Cecilia J. Tsang
Assistant Examiner—Bennett Celsa
Attorney, Agent, or Firm—Catherine D. Fitch; Melvin Winokur

[57] ABSTRACT

Compounds of the formula

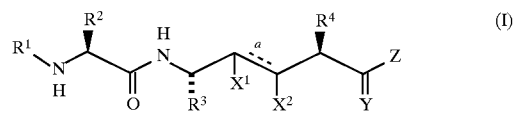

are inhibitors of peptide binding to major histocompatibility complex type II proteins and may be used in the treatment and prevention of autoimmune diseases including: rheumatoid arthritis, Type I diabetes, multiple sclerosis, lupus erythematosis, Graves disease and pemphigus. The present invention also provides novel compositions, methods of treatment employing compounds of the present invention and methods of manufacture of the compounds of structural formula (I).

14 Claims, No Drawings

OTHER PUBLICATIONS

Jones et al., Abstracts of the 25th Nat'l Medicinal Chemistry Symposium, Jun. 18–22, 1996, Ann Arbor, MI., "The development of peptidomimetic inhibitors of the binding of antigenic peptide to MHC Class II".

Adams et al., Abstracts of 25th Nat'l Medicinal Chemistry Symposium, University of Michigan, Ann Arbor, MI, Jun. 18–22, 1996, Abstract No. 98, "The development of small molecule inhibitors of the binding of antigenic peptide to MHC Class II".

Jones et al., Abstracts of the XIVth Int'l Symposium on Medicinal Chemistry, Maastricht, The Netherlands, Sep. 8–12, 1996, "Inhibition of MHC Class II ligation by peptidomimetics: prospects for antigen specific immunosuppression".

Acton III et al., Tetra. Lett., vol. 37, No. 25, pp. 4319–4322 (1996), "Synthesis and derivatization of a versatile alpha–substituted lactam dipeptide isostere".

Acton III et al., C&EN, Feb. 19, 1996, 211th ACS Nat'l Meeting, New Orleans, Mar. 24–28, 1996, "alpha–Allyl lactam dipeptide isosteres: Synthesis and utility of a versatile intermediate".

Rusiecki et al., Abstracts of the 20th IUPAC Symposium on the Chemistry of Natural Products, Chicago, IL, Sep. 15–20, 1996, "Modular synthesis of tripeptide inhibitors of MHC Class II".

INHIBITORS OF PEPTIDE BINDING TO MHC CLASS II PROTEINS

This application is a continuation of Provisional Application 60/005,994 filed Oct. 30, 1995.

FIELD OF THE INVENTION

The present invention provides novel compounds, novel compositions, methods of their use and methods of their manufacture, where such compounds are generally pharmacologically useful as agents in therapies whose mechanism of action rely on the inhibition of peptide binding to major histocompatibility complex (MHC) class II molecules, and more particularly useful in therapies for the treatment and prevention of autoimmune diseases.

BACKGROUND OF THE INVENTION

A basic function of the immune system is to distinguish self from non-self, an activity carried out primarily by T cells. Failure of mechanisms which control the tolerance of T cells to self antigens and the prevention of activation of T cells by self antigens may lead to autoimmunity. In individuals afflicted with autoimmune diseases, an increased frequency of alleles for specific human leukocyte antigens (HLAs) are found, and it is believed that the disease-associated HLA molecules have the ability to bind the autoantigen and present it to T cells, thereby inducing and/or maintaining the autoimmune process. Currently available immunosuppressive drugs are inadequate because of limited efficacy, lack of selectivity and considerable toxicity.

The present invention is directed to compounds which inhibit the binding of peptides to the major histocompatibility complex class II, a more selective target for therapeutic treatment and prevention of autoimmune diseases. Major histocompatibility complex class II molecules (MHC class II) are cell-surface glycoproteins that bind antigenic peptide fragments and display them at the cell surface to CD4-positive helper T-cells. The action of these molecules forms part of a pathway of the immune system for identifying and responding to foreign antigens. In brief, antigen presenting cells internalize foreign proteins. Once internalized, the proteins are proteolytically degraded and short sequences of the degraded proteins are bound to MHC class II molecules in an endosomal compartment. These complexes of the short sequences bound to the MHC Class II molecule are then exposed on the cell surface where they initiate a series of immunogenic events.

MHC Class II proteins are synthesized and assembled in the endoplasmic reticulum as trimers composed of highly polymorphic α and β-chain polypeptides and a non-polymorphic invariant chain polypeptide. The invariant chain prevents the premature binding of peptides to MHC class II. In addition, the invariant chain contains a sequence that targets the α/β heterodimer into the low pH, protease-rich endosomal compartment. In this compartment, the invariant chain is removed, leaving the MHC class II α/β heterodimers free to bind antigenic peptides.

Both class I and class II histocompatibility proteins have different domain organizations but similar structures, with two membrane-proximal immunoglobulin-like domains and a membrane-distal peptide-binding site formed by an eight stranded β-sheet and two α-helical regions. Polymorphic residues in both class I and II proteins are clustered in the peptide-binding region and are responsible for the different peptide specificities observed for different histocompatibility proteins. Class I histocompatibility proteins are specific for peptides of defined length, usually 8–10 residues and have allele-specific binding motifs characterized by strong preferences for a few side chains at some positions in the peptide, and wide tolerance for many side chains at the other positions. Class II histocompatibility proteins bind longer peptides with no apparent restriction on peptide length. Class II proteins also have allele specific motifs, which have been more difficult to characterize because of the difficulty in aligning peptide sequences of different lengths.

The mechanism of peptide binding to class II histocompatibility proteins has not been clearly defined. The 3.3 angstrom crystal structure of the human class II histocompatibility protein HLA-DR1 showed that bound peptide extended out the ends of the binding site, but interpretation of HLA-peptide interactions was complicated by the presence of a mixture of endogenous peptides in the peptide-binding site. Brown et al., Nature 364:33–39 (1993).

Stern et al. determined the refined 2.75 angstrom structure of the HLA-DR 1/HA peptide complex showing that the peptide binds as a straight extended chain with a pronounced twist. Nature 368:215–221(1994). Hydrogen bonds between main-chain atoms along the peptide and HLA-DR1 residues from the α-helical regions and the β-sheet provide a component to the binding interaction that is independent of peptide sequence. Twelve of the hydrogen bonds involve residues conserved in most human and mouse class II alleles, and suggest a universal method for peptide binding by class II histocompatibility proteins. Five side chains of the HA peptide are accommodated by polymorphic pockets in the HLA-DR1 binding site. These pockets appear to determine the peptide specificity of different class II proteins.

Antigen presenting cells (APCs) expressing MHC class II molecules capture proteins from extracellular fluids. APCs can take up antigens through surface immunoglobulin receptors, through $F_c$ receptor-mediated internalization of antibody/antigen complexes, or through bulk-phase endocytosis. Internalized antigens are then transported to endosomal compartments where they are digested into peptide fragments. A subset of these peptides can associate with a specific binding groove at the interface of MHC class II α and β-chain heterodimers. Most of the polymorphisms in these proteins are located within this binding groove, so that each different MHC class II allele can bind a distinct, but overlapping, subset of antigenic peptides. MHC class II/peptide complexes are then transported to the cell surface where they are recognized by T-cell receptors (TCRs) on CD4-positive T-cells. This process is pivotal for the generation of both humoral and cellular immune responses.

Three genetic loci within the human MHC encode class II antigen-presenting molecules: HLA-DP, HLA-DQ, and HLA-DR. These loci are highly polymorphic. For instance, there are over 30 DRβ alleles in the human population. Since each individual expresses only a small number of different histocompatibility proteins, each histocompatibility protein must be able to bind a large number of different peptides in order to ensure an immune response against many possible pathogens. The extensive polymorphism of histocompatibility genes may be the result of selection of alleles that can present peptides from particular pathogens.

The inheritance of particular MHC class II alleles is linked to susceptibility to many autoimmune diseases. A prominent example of this is susceptibility to rheumatoid arthritis (RA) which is genetically associated with a small subset of related DR alleles (DR4Dw4, DR4Dw4, and DR1). See, Skinner et al., Annals of the Rheumatic Diseases 53:171–177 (1994). Over 90% of RA patients possess at least one of these 3 DR alleles compared to 27% in an age-matched control group.

Autoimmune conditions are thought to involve the T-cell recognition of self-components by MHC Class II proteins, a situation which is normally avoided. This presentation generates an undesirable immune response to self. Since the sole function of MHC class II molecules is to present peptide antigens, the present invention is concerned with compounds which interfere with the binding of peptides to MHC class II molecules and a method of treating and preventing autoimmune diseases employing such compounds which interfere with the binding of peptides to MHC class II molecules associated with disease. Specifically blocking the formation of the MHC Class II/self-peptide complex is a manner of disrupting the aberrant process of the autoimmune disorder without globally depressing immune function. Hurtenbach et al., J. Exp. Med. 177:1499–1504 (1993) demonstrated that treatment with MHC class II complex-blocking peptide prevented autoimmune diabetes in non-obese diabetic mice. Further, Guery et al., J. Exp. Med. 177:1461–1468 (1993) administered MHC class II binding peptides to mice and showed suppression of induction of T cell antibody responses. The binding inhibitors of the present invention may prevent the presentation of self-peptides to autoreactive T-cells that drive the disease process. An advantage of the immunotherapy and immunotherapeutic agents of the present invention is that they are very selective agents, targeting only certain alleles of MHC Class II, which may minimize the risk of opportunistic infections during long term treatment. Although competition for MHC binding among peptides is known, no non-peptide (or pseudopeptide) inhibitor of MHC Class II binding has been known. Due to the inherent pharmacological limitations of peptides, particularly within a system that involves proteolytic degradation of proteins, the compounds of the present invention having less peptidic character may present a useful avenue for therapy.

SUMMARY OF THE INVENTION

The novel compounds of this invention are those of structural formula I:

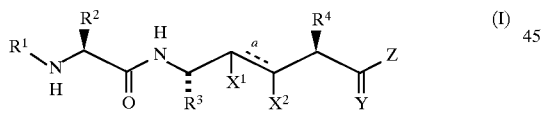

or a pharmaceutically acceptable salt or ester thereof, that inhibit peptide binding to MHC Class II proteins. As inhibitors of binding to MHC Class II proteins, the compounds of the present invention may be used in the treatment and prevention of autoimmune diseases, including rheumatoid arthritis, Type I diabetes, multiple sclerosis, lupus erythematosis, Graves disease and pemphigus.

There is no precedent in the literature for inhibition of MHC Class II proteins by nonpeptides or pseudopeptides.

Therefore it is an object of this invention to provide compounds that have activity in the inhibition of peptide binding to MHC Class II proteins. It is an additional object of this invention to provide methods of using the compounds of formula I for the treatment of autoimmune conditions such as rheumatoid arthritis, Type I diabetes, multiple sclerosis, lupus erythematosis, Graves disease and pemphigus. It is a further object of this invention to provide pharmaceutical compositions for the compounds of formula I. Still another object of the present invention is to provide a method for in vitro inhibition of peptide binding of MHC Class II proteins.

DETAILED DESCRIPTION OF THE INVENTION

The novel compounds of this invention have the general structural formula I:

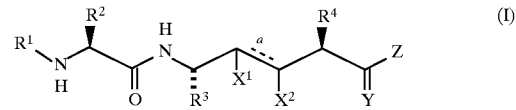

or a pharmaceutically acceptable salt or ester thereof wherein:

the bond represented by the dotted line "a" is selected from a single bond and a double bond;

when "a" represents a double bond $X^1$ and $X^2$ are each hydrogen;

when "a" represents a single bond, $X^1$ and $X^2$ are each $H_2$, or $X^1$ and $X^2$ together are $CH_2$, forming a cyclopropane ring with the "a" bond;

Z is selected from:
(a) $NH_2$,
(b) $NHR^7$,
(c) OH, and
(d) $OR^7$;

Y is selected from:
(a) O, and
(b) H,H;

$R^1$ is

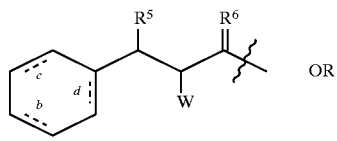 OR

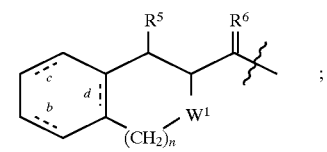 ;

$R^2$ is:
(a) $C_{1-8}$ alkyl, unsubstituted or substituted with one or two substituents selected from:
(1) —$CONHR^8$,
(2) —$COOR^8$,
(3) —COOH,
(4) OH,
(5) $C_5$-alkoxy,
(6) —$NHC(O)R^8$,
(7) pyridyl,
(8) $NH_2$, and
(9) $NHR^8$;

$R^3$ is $C_{2-6}$ alkyl, unsubstituted or substituted with one or two substituents selected from:
(a) $C_{3-8}$cycloalkyl,
(b) aryl,
(c) $CF_3$, and
(d) halogen;

$R^4$ is $C_{2-6}$ alkyl, unsubstituted or substituted with one or two substituents selected from:
(a) $C_{3-8}$cycloalkyl, (b) aryl,
(c) $CF_3$, and
(d) halogen;

$R^5$ is selected from:
(a) hydrogen, and
(b) $C_{1-5}$ alkyl, unsubstituted or substituted with one to three substituents selected from:
(1) $C_{3-8}$cycloalkyl,
(2) aryl,
(3) OH,
(4) $NH_2$, and
(5) halogen;

$R^6$ is selected from:
(a) two hydrogens,
(b) hydrogen and $C_{1-5}$ alkyl, wherein the $C_{1-5}$ alkyl is unsubstituted or substituted with one to three substituents selected from:
(1) $C_{3-8}$cycloalkyl,
(2) aryl,
(3) OH,
(4) $NH_2$, and
(5) halogen, and
(c) =O (carbonyl);

$R^7$ is selected from:
(a) hydrogen, and
(b) $C_{1-5}$ alkyl, unsubstituted or substituted with one or two substituents selected from:
(1) $C_{3-8}$cycloalkyl,
(2) aryl,
(3) OH,
(4) $NH_2$, and
(5) halogen;

at each occurrence, $R^8$ is independently selected from: $C_{1-3}$alkyl and aryl;

the bonds represented by the dotted lines "b", "c", and "d" are each independently selected from a single bond and a double bond;

n is selected from zero, 1 and 2;

W is selected from:
(a) hydrogen,
(b) $NH_2$,
(c) $NHR^5$, and
(d) $NHCOR^5$;

$W^1$ is selected from:
(a) O,
(b) NH,
(c) $NR^5$, and
(d) $NCOR^5$;

aryl is selected from:
(a) phenyl,
(b) naphthyl,
(c) indenyl,
(d) thiophenyl,
(e) benzothiophenyl,
(f) furanyl,
(g) benzofuranyl,
(h) pyrollyl,
(i) indolyl, and
(j) pyridyl;

wherein the aryl group may be unsubstituted or substituted with one to three substituents selected from:
(1) $C_{1-4}$ alkyl,
(2) $C_{1-4}$ alkoxy,
(3) halogen, and
(4) hydroxy.

As used herein "alkyl" is intended to include both branched- and straight-chain saturated aliphatic hydrocarbon groups having the specified number of carbon atoms, e.g, methyl, ethyl, propyl, butyl, pentyl, hexyl, heptyl, octyl, nonyl, decyl and isomers thereof such as isopropyl, isobutyl, sec-butyl, tert-butyl, isopentyl, isohexyl, etc. "Alkoxy" represents an alkyl group having the indicated number of carbon atoms attached through an oxygen bridge, e.g. methoxy, ethoxy, propyloxy, isopropoxy, etc. "Alkoxycarbonyl" represents a group of the form "alkyl-O—C(O)—" wherein the indicated number of carbon atoms refers to those of the alkyl residue. "Acyl" represents an alkyl group having the indicated number of carbon atoms attached through a —C(O)— bridge. "Sulfonyl" represents an alkyl group having the indicated number of carbon atoms attached through a —$SO_2$— bridge.

The terms halogen and halo refer to F, Cl, Br and I.

The heterocyclic or aryl ring may be attached to the structural formula I at any nitrogen or carbon atom in the ring which results in the creation of a stable, uncharged structure.

Combinations of substituents and/or variables are permissible only if such combinations result in stable compounds.

The present invention is illustrated by the following compounds:

EtOCO-Phe Lys Abu ψ[E,CH=CH]Nva-$NH_2$,
EtOCO-Cha Lys Abu ψ[E,CH=CH]Nva-$NH_2$,
EtOCO-Cha Lys Nva ψ[E,CH=CH]Leu-$NH_2$,
EtOCO-Cha Lys Nva ψ[CH2CH2]Leu-$NH_2$,
EtOCO-Cha Lys Nva ψ[E,CH=CH]Nle-$NH_2$,
EtOCO-Cha Orn Nva ψ[E,CH=CH]Nle-$NH_2$,
EtOCO-Cha Arg Nva ψ[E,CH=CH]Nle-$NH_2$,
EtOCO-Cha Lys Nva ψ[trans,cPr]Nle-$NH_2$,
cHx(CH2)3-Lys Nva ψ[E,CH=CH]Nle-$NH_2$,
[3R-(3-cyclohexyl-3-methyl)propyl]-Lys Nva ψ[E,CH=CH]Nle-$NH_2$,
[trans-(1S,2R)-2-cyclohexylcyclopropyl-1-methyl]-Lys Nva ψ[E,CH=CH]Nle-$NH_2$,
[(2R)-(1,2,3,4-Tetrahydronaphthyl)methyl]-Lys Nva ψ[E,CH=CH]Nle-$NH_2$,
[(2S)-(1,2,3,4-Tetrahydronaphthyl)methyl]-Lys Nva ψ[E,CH=CH]Nle-$NH_2$,
[(2R,4aR,8aS)-Octahydrylnaphthylmethyl]-Lys Nva ψ[E,CH=CH]Nle-$NH_2$,
[(2R,4aS,8aR)-Octahydrylnaphthylmethyl]-Lys Nva ψ[E,CH=CH]Nle-$NH_2$,
[(2R,4aS,8aS)-Octahydrylnaphthylmethyl]-Lys Nva ψ[E,CH=CH]Nle-$NH_2$,
[(2R,4aR,8aR)-Octahydrylnaphthylmethyl]-Lys Nva ψ[E,CH=CH]Nle-$NH_2$,
cHx(CH2)3-Lys Nva ψ[E,CH=CH]Nle-OEt,
cHx(CH2)3-Lys Nva ψ[E,CH=CH]Norleucinol,
cHx(CH2)3-(ε-Nic)Lys Nva ψ[E,CH=CH]Nle-$NH_2$,
cHx(CH2)3-(3-Pyr)Ala Nva ψV[E,CH=CH]Nle-$NH_2$, In one class of this invention are compounds further limited to those wherein:

EtOCO-Phe Lys Abu ψ[E,CH=CH]Nva-$NH_2$,
EtOCO-Cha Lys Abu ψ[E,CH=CH]Nva-$NH_2$,
EtOCO-Cha Lys Nva ψ[E,CH=CH]Leu-$NH_2$,
EtOCO-Cha Lys Nva ψ[CH2CH2]Leu-$NH_2$,
EtOCO-Cha Lys Nva ψ[E,CH=CH]Nle-$NH_2$,
EtOCO-Cha Lys Nva ψ[trans,cPr]Nle -$NH_2$,
cHx(CH2)3-Lys Nva ψ[E,CH=CH]Nle-$NH_2$,
[(2R)-(1,2,3,4-Tetrahydronaphthyl)methyl]-Lys Nva ψ[E,CH=CH]Nle-$NH_2$,
[(2S)-(1,2,3,4-Tetrahydronaphthyl)methyl]-Lys Nva ψ[E,CH=CH]Nle-$NH_2$,
[(2R,4aS,8aR)-Octahydrylnaphthylmethyl]-Lys Nva ψ[E,CH=CH]Nle-$NH_2$,

[(2R,4aR,8aS)-Octahydrylnaphthylmethyl]-Lys Nva ψ[E, CH═CH]Nle-NH$_2$,
cHx(CH2)3-Lys Nva ψ[E,CH═CH]Norleucinol,
cHx(CH2)3-(ε-Nic)Lys Nva ψ[E,CH═CH]Nle-NH$_2$,
cHx(CH2)3-(3-Pyr)Ala Nva ψ[E,CH═CH]Nle-NH$_2$, Examples of compounds within this class include, but are not limited to, the following:

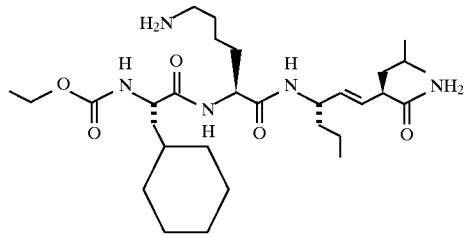

EtOCO—Cha Lys Nva ψ[E, CH═CH]Leu—NH$_2$

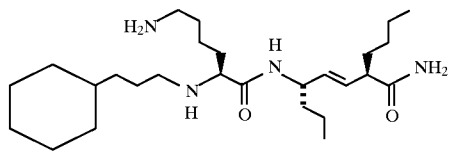

cHx(CH2)$_3$—Lys Nva ψ[E, CH═CH]Nle—NH$_2$

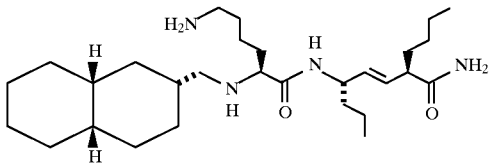

[(2R, 4aR, 8aS)-Octahydronaphthyl-2-methyl-Lys Nva ψ[E, CH═CH]Leu—NH$_2$

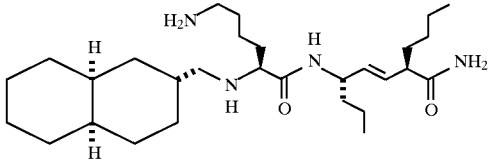

[(2R,4aS,8aR)Octahydronaphthyl-2-methyl]-Lys Nva ψ[E,CH═CH]Leu—NH$_2$

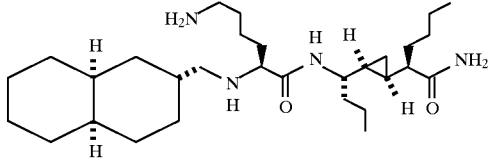

[(2R,4aS,8aR)Octahydronaphthyl-2-methyl]-Lys Nva ψ[trans, cPr]Leu—NH$_2$

In one embodiment of the present invention,

Z is selected from:
(a) NH$_2$,
(b) NHR$^7$,
(c) OH, and
(d) OR$^7$;

Y is selected from:
(a) O, and
(b) H,H;

R$^1$ is

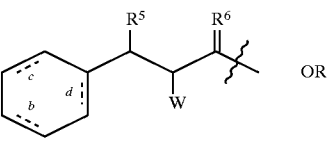   OR

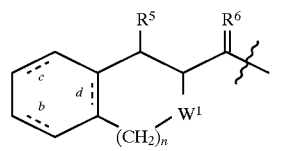  ;

R$^2$ is:
(a) C$_{1-8}$ alkyl, unsubstituted or substituted with one substituent selected from:
(1) —CONHR$^8$,
(2) —COOR$^8$,
(3) —COOH,
(4) OH,
(5) alkoxy,
(6) —NHC(O)R$^8$,
(7) pyridyl,
(8) NH$_2$, and
(9) NHR$^8$;

R$^3$ is C$_{2-6}$ alkyl, unsubstituted or substituted with one substituent selected from:
(a) C$_{3-8}$cycloalkyl,
(b) aryl,
(c) CF$_3$, and
(d) halogen;

R$^4$ is C$_{2-6}$ alkyl, unsubstituted or substituted with one substituent selected from:
(a) C$_{3-8}$cycloalkyl,
(b) aryl,
(c) CF$_3$, and
(d) halogen;

R$^5$ is selected from:
(a) hydrogen, and
(b) C$_{1-5}$ alkyl;

R$^6$ is selected from:
(a) two hydrogens,
(b) hydrogen and C$_{1-5}$ alkyl, and
(c) ═O (carbonyl);

R$^7$ is selected from:
(a) hydrogen, and
(b) C$_{1-5}$ alkyl, unsubstituted or substituted with one substituent selected from:
(1) C$_{3-8}$cycloalkyl,
(2) aryl,
(3) OH,
(4) NH$_2$, and
(5) halogen;

at each occurrence, R$^8$ is independently selected from:
C$_{1-3}$alkyl and aryl;

the bonds represented by the dotted lines "b", "c", and "d" are all double bonds or are all single bonds;

n is selected from zero, 1 and 2;

W is selected from:
(a) hydrogen,
(b) NH$_2$,
(c) NHR$^5$, and
(d) NHCOR$^5$;

$W^1$ is selected from:
(a) O,
(b) NH,
(c) $NR^5$, and
(d) $NCOR^5$;

aryl is selected from:
(a) phenyl,
(b) naphthyl,
(c) indenyl,
(d) thiophenyl,
(e) benzothiophenyl,
(f) furanyl,
(g) benzofuranyl,
(h) pyrollyl,
(i) indolyl, and
(j) pyridyl;

wherein the aryl group may be unsubstituted or substituted with one to three substituents selected from:
(1) $C_{1-4}$ alkyl,
(2) $C_{1-4}$ alkoxy,
(3) halogen, and
(4) hydroxy.

In another embodiment of the instant invention are compounds of formula I wherein:
"a" is a double bond; and
$X^1$ and $X^2$ are each hydrogen.

In one class of the compounds of this embodiment, "b", "c" and "d" each represent single bonds,
$R^1$ is 3-cyclohexyl propyl:

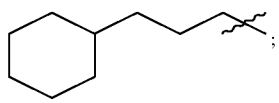

$R^2$ is $C_{1-8}$ alkyl, unsubstituted or substituted with one substituent selected from:
(1) —$CONHR^8$,
(2) —$NHC(O)R^8$,
(3) pyridyl,
(4) $NH_2$, and
(5) $NHR^8$, $R^3$ and $R^4$ each represent unsubstituted $C_{2-6}$ alkyl; and at each occurrence, $R^8$ is independently selected from: $C_{1-3}$alkyl, and aryl.

In one subclass of this class of the present invention, $R^3$ is ethyl or propyl and $R^4$ is propyl, butyl or isobutyl.

In another embodiment of the instant invention are compounds of formula I wherein:
"a" is a single bond and $X^1$ and $X^2$ are each $H_2$.

In one class of the compounds of this embodiment, "b", "c" and "d" each represent single bonds,
$R^1$ is 3-cyclohexyl propyl:

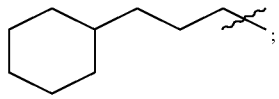

$R^2$ is $C_{1-8}$ alkyl, unsubstituted or substituted with one substituent selected from:
(1) —$CONHR^8$,
(2) —$NHC(O)R^8$,
(3) pyridyl,
(4) $NH_2$, and
(5) $NHR^8$;

$R^3$ and $R^4$ each represent unsubstituted $C_{2-6}$ alkyl; and at each occurrence, $R^8$ is independently selected from: $C_{1-3}$alkyl, and aryl.

In one subclass of this class of the present invention, $R^3$ is ethyl or propyl and $R^4$ is propyl, butyl or isobutyl.

In still another embodiment of the instant invention are compounds of formula I wherein:
"a" is a single bond and $X^1$ and $X^2$ together are $CH_2$, forming a trans cyclopropane ring with the "a" bond;

In one class of the compounds of this embodiment, "b", "c" and "d" each represent single bonds;
$R^2$ is:
(a) $C_{1-8}$ alkyl, unsubstituted or substituted with one substituent selected from:
(1) —$CONHR^8$,
(2) —$NHC(O)R^8$,
(3) pyridyl,
(4) $NH_2$, and
(5) $NHR^8$;

$R^3$ and $R^4$ each represent unsubstituted $C_{2-6}$ alkyl;
$R^5$ is selected from:
(a) hydrogen, and
(b) unsubstituted $C_{1-5}$ alkyl;
$R^6$ is selected from:
(a) hydrogen, and
(b) unsubstituted $C_{1-5}$ alkyl;

at each occurrence, $R^8$ is independently selected from: $C_{1-3}$alkyl, and aryl; and W is hydrogen.

In one subclass of this class of the present invention, $R^3$ is ethyl or propyl and $R^4$ is propyl, butyl, or isobutyl.

The compounds of the present invention are named according to the system described below, based on standard usage from the *Journal of Biological Chemistry*, and IUPAC's Nomenclature standards. The compounds of the present invention are named by reference to a tetrapeptide. The residues of this tetrapeptide on which the nomenclature for the compounds of the present invention are numbered as indicated below;

P1-P2-P3-P4 where "PX" represents the amino acid in the "xth" position in the tetrapeptide. P1 is the amino terminal residue, and may be protected by a group referred to as a "cap". P4 is the carboxy terminal residue. In compounds of the present invention the dipeptide isostere, for example Nvaψ[E, CH=CH]Leu, substitutes for two amino acid residues, P3 and P4.

When an amino acid is incorporated into the structure, the name of the amino acid residue is given as three letter amino acid code, or as a generally accepted abbreviation. For general usage reference was made to: Amino Acid and Peptide Nomenclature *J. Biol. Chem* 260, 14–42 and IUPAC-IUB Nomenclature recommendations Name Format: Names are given as the Amino terminus "cap", abbreviated as described below, followed by a hyphen and the three letter code of the first residue (or the abbreviation for the replacement residue), followed by a space, etc. After the last amino acid residue, or replacement, a hyphen, followed by the moiety positioned at the carboxy terminus of the analogous tetrapeptide, i.e. —NH2, —OH, —OEt.

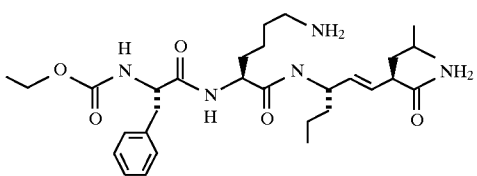

| Trivial Name | EtOCO— | Phe | Lys | Navψ[E,CH=CH]Leu | —NH2 |
|---|---|---|---|---|---|
| | Cap | P1 | P2 | P3–P4 | "P5" |
| | EtOCO— | Phe | Lys | Nvaψ[E,CH=CH]Leu | —NH2 |

Unconventional Residues

For reduced terminus, alinol, leucinol, etc. often the name of the residue is spelled out.

Non-amino acid residues are generally named as one line alphanumeric structures constructed from accepted abbreviations. cHx(CH2)3-.

Amide Bond Isosteres

Analogs of peptides in which the amide bond is replaced with some other joining group are represented by the letter psi, ψ followed by the joining group in square brackets, placed between the residue symbols where the substitution is made. These are generally entered as one residue. Isosteres are single enantiomers and stereochemistry for the relevant center corresponds to the natural L isomer unless denoted otherwise.

-Alaψ[E,CH=CH]Ala- —HN—CH(CH₃)—CH=CH—CH(CH₃)—CO- -Alaψ[CH₂NH] Etc.

Protecting Groups, R Groups and Reagents

Generally accepted abbreviations are employed. A representative list is included below

| Name | Abbreviation(s) |
|---|---|
| Alkyls | usual 2–3 letters: Et, Pr, Bu, iBu |
| Benzoyl | Bz |
| Benzyl | Bzl |
| Benzyloxycarbonyl | CBZ, Z |
| Cyclohexyl | cHx |

Other Naming conventions

Caps Entered as amino terminal capping residue by Structure, or name

Alkyls, Acyls(non amino acid), ureas:

Alkyls-Simple residues as usual iPr, Et etc. For nontrivial; One line notation of structure; cHx(CH₂)₃

Acyls-Similarly Ac, EtOCO as usual. Nontrivial; 3-PyrCO (3-pyridyl-CO), 1-NphCO (1-Naphthyl-CO).

Ureas-BzlNHCO—, etc.

Cha Cyclohexyl alanine.

The compounds of the present invention are of substantially non-peptide character, yet inhibit peptide binding MHC Class II proteins. Because the compounds of the present invention have substantially reduced peptide character relative to known inhibitors, the compounds of the present invention will be more likely to penetrate cellular membranes to access the Class II loading compartment within the cell, where competition for peptide binding is thought to occur. They are also likely to be more stable than peptides in the proteolytic environment of the endosomal compartment and hence better able to compete with the endogenous peptides. Based on knowledge within the art regarding peptide versus nonpeptide pharmacology, the compounds of the present invention are expected to have better oral bioavailability and longer in vivo half life than intact peptides.

Also included within the scope of this invention are pharmaceutically acceptable salts of the compounds of formula I, where a basic or acidic group is present on the structure.

The compounds of the present invention may be administered in the form of pharmaceutically acceptable salts. The term "pharmaceutically acceptable salt" is intended to include all acceptable salts such as acetate, lactobionate, benzenesulfonate, laurate, benzoate, malate, bicarbonate, maleate, bisulfate, mandelate, bitartrate, mesylate, borate, methylbromide, bromide, methylnitrate, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutamate, stearate, glycollylarsanilate, sulfate, hexylresorcinate, subacetate, hydrabamine, succinate, hydrobromide, tannate, hydrochloride, tartrate, hydroxynaphthoate, teoclate, iodide, tosylate, isothionate, triethiodide, lactate, panoate, valerate, and the like which can be used as a dosage form for modifying the solubility or hydrolysis characteristics or can be used in sustained release or prodrug formulations. Depending on the particular functionality of the compound of the present invention, pharmaceutically acceptable salts of the compounds of this invention include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris (hydroxymethyl)aminomethane, and tetramethylammonium hydroxide. These salts may be prepared by standard procedures, e.g. by reacting a free acid with a suitable organic or inorganic base. Where a basic group is present, such as amino, an acidic salt, i.e. hydrochloride, hydrobromide, acetate, pamoate, and the like, can be used as the dosage form.

Also, in the case of an acid (—COOH) or alcohol group being present, pharmaceutically acceptable esters can be employed, e.g. acetate, maleate, pivaloyloxymethyl, and the like, and those esters known in the art for modifying solubility or hydrolysis characteristics for use as sustained release or prodrug formulations.

When any variable (e.g., X, Y, R¹, etc.) occurs more than one time in any constituent or in formula I, its definition on each occurrence is independent of its definition at every other occurrence. Also, combinations of substituents and/or variables are permissible only if such combinations result in stable compounds.

Some of the crystalline forms for compounds of the present invention may exist as polymorphs and as such are intended to be included in the present invention. In addition, some of the compounds of the instant invention may form solvates with water or common organic solvents. Such solvates are encompassed within the scope of this invention.

The term "therapeutically effective amount" means that amount of a drug or pharmaceutical agent that will elicit the biological or medical response of a tissue, system, animal or human that is being sought by a researcher, veterinarian, medical doctor or other clinician, which includes alleviation of the symptoms of the disorder being treated. The novel methods of treatment of this invention are for disorders known to those skilled in the art. The term "mammal" includes humans.

The present invention has the objective of providing methods of treating and preventing autoimmune diseases including: rheumatoid arthritis, Type I diabetes, multiple sclerosis, lupus erythematosis, Graves disease and pemphigus by oral, systemic, parenteral or topical administration of the novel compounds of formula I either alone or in combination with other agents useful in treating autoimmune diseases. For the treatment of rheumatoid arthritis such agents which may be used in combination with the novel compounds of structural formula (I) include, but are not limited to: aspirin; NSAIDs including fenoprofen, tolmetin, sulindac, meclofenamate, indomethacin, ibuprofen, naproxen, ketoprofen, piroxicam, flurbiprofen, and diclofenac; gold sodium thiomalate; aurothioglucose; auranofin; penicillamine; hydroxychloroquine; sulfasalazine, corticosteroids; methotrexate; azathioprine; and cyclophosphamide. For the treatment of type 1 diabetes such agents which may be used in combination with the novel compounds of structural formula (I) include, but are not limited to: insulin therapy. For the treatment of multiple sclerosis such agents which may be used in combination with the novel compounds of structural formula (I) include, but are not limited to: prednisone, dexamethazone, azathioprine, copolymer 1, cyclophosphamide, interferon, plasmapheresis, and baclofen. For the treatment of lupus erythematosis, such agents which may be used in combination with the novel compounds of structural formula (I) include, but are not limited to: antimalarials such as hydroxychloroquinine, chloroquine, and quinacrine; prednisone and methyl prenisolone; and cyclophosphamide. For the treatment of pemphigus, such agents which may be used in combination with the novel compounds of structural formula (I) include, but are not limited to: systemic corticosteroids, prednisone, methotrexate, cyclophosphamide and azathioprine.

The present invention also has the objective of providing suitable topical, oral, systemic and parenteral pharmaceutical formulations for use in the novel methods of treatment and prevention of the present invention. The term "treatment" is intended to include ameliorating the autoimmune symptoms and/or arresting the progression of an autoimmune disease in an individual known to be, or believed to be suffering from an autoimmune disease. The term "prevention" is intended to include ameliorating the underlying cause of an autoimmune condition in an individual who may not have begun to experience recognizable symptoms of an autoimmune condition, and arresting the progress of an autoimmune disease in a patient who has not begun to experience recognizable symptoms of an autoimmune condition. The term "administration of" or "administering a" compound should be understood to mean providing a compound of the invention or a prodrug of a compound of the invention to the individual in need of treatment. The compositions containing the present compounds as the active ingredient for use in the treatment of the above-noted conditions can be administered in a wide variety of therapeutic dosage forms in conventional vehicles for systemic administration. For example, the compounds can be administered in such oral dosage forms as tablets, capsules (each including timed release and sustained release formulations), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form, all using forms well known to those of ordinary skill in the pharmaceutical arts.

The compounds of the present invention may be used to prepare a medicament or agent useful in the treatment of autoimmune diseases, including: Graves' disease, rheumatoid arthritis, Type I diabetes, lupus erythematosis, pemphigus and multiple sclerosis.

The daily dosage of the products may be varied over a range from 0.01 to 1,000 mg per adult human/per day. For oral administration, the compositions are preferably provided in the form of tablets containing from 0.01 to 1,000 mg, preferably 0.01, 0.05, 0.1, 0.5, 1.0, 2.5, 5.0, 10.0, 15.0, 25.0, and 50.0 milligrams of the active ingredient for the symptomatic adjustment of the dosage to the patient to be treated. An effective amount of the drug is ordinarily supplied at a dosage level of from about 0.0002 mg./kg. to about 50 mg./kg. of body weight per day. The range is more particularly from about 0.001 mg./kg. to 7 mg./kg. of body weight per day.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

For the treatment and prevention of autoimmune diseases, the compounds of the present invention may be administered in a pharmaceutical composition comprising the active compound in combination with a pharmaceutically acceptable carrier adapted for topical administration. Topical pharmaceutical compositions may be, e.g., in the form of a solution, cream, ointment, gel, lotion, shampoo or aerosol formulation adapted for application to the skin. These topical pharmaceutical compositions containing the compounds of the present invention ordinarily include about 0.005% to 5% by weight of the active compound in admixture with a pharmaceutically acceptable vehicle.

For the treatment and prevention of autoimmune diseases, the compounds of the present invention may be used together with agents known to be useful in treating autoimmune disease, discussed previously.

For combination treatment with more than one active agent, where the active agents are in separate dosage formulations, the active agents can be administered concurrently, or they each can be administered at separately staggered times.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter or arrest the progress of the condition. Optimal precision in achieving concentration of drug within the range that yields efficacy without toxicity requires a regimen based on the kinetics of the drug's availability to target sites. This involves a consideration of the distribution, equilibrium, and elimination of a drug.

In the methods of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like. Other dispersing agents which may be employed include glycerin and the like. For parenteral administration, sterile suspensions and solutions are desired. Isotonic preparations which generally contain suitable preservatives are employed when intravenous administration is desired.

Topical preparations containing the active drug component can be admixed with a variety of carrier materials well known in the art, such as, e.g., alcohols, aloe vera gel, allantoin, glycerine, vitamin A and E oils, mineral oil, PPG2 myristyl propionate, and the like, to form, e.g., alcoholic solutions, topical cleansers, cleansing creams, skin gels, skin lotions, and shampoos in cream or gel formulations. See, e.g., EP 0 285 382.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydro-pyrans, polycyanoacrylates and cross-linked or amphipathic block copolymers of hydrogels.

The compounds of the present invention can be prepared readily according to the following Schemes and Examples or modifications thereof using readily available starting materials, reagents and conventional synthesis procedures. In these reactions, it is also possible to make use of variants which are themselves known to those of ordinary skill in this art, but are not mentioned in greater detail.

General Synthetic Access to Xaaψ[E,CH═CH]Xaa and Xaaψ[cPr, trans]Xaa dipeptide Isosteres The compounds of the present invention are receptor binding substrates intended to mimic four of the amino terminus proximal residues of known biologically relevant ligands. The analogs described are therefore tetrapeptide mimics, or tetrapeptide register peptidomimetics. Synthetic methods involve the synthesis of the enantiomerically pure Xaaψ[E,CH═CH]Xaa and Xaaψ[cPr,trans]Xaa dipeptide isosteres and the elaboration of these dipeptide mimics to the tetrapeptide register. Elaboration of the dipeptide isostere is by normal peptide type coupling chemistry, and known alkylation methods.

The analogs discussed here are in principal accessible by any of several methods which are known in the literature for the synthesis of Xaaψ[E,CH═CH]Xaa dipeptide olefin isosteres. Some representative examples are;

1) Wai, J. S.; Thorsten, E. F.; Embrey, M. W. *Tetrahedron Letters* 1995, 36, 3461.
2) McKinnney, J. A.; Eppley, D. F.; Keenan, R. M. *Tetrahedron Letters* 1994,35(33), 5985–5988.
3) Beresis, R.; Panek, J. S. *Biorg. Med. Chem. Letters* 1993, 3(8) 1609–1614.
4) Allmendinger, T.; Furet, P.; Hingerbühler, E. *Tetrahedron Letters,* 1990, 31(50) 7297–7300.
5) Allmendinger, T.; Felder, E.; Hingerbühler, E. *Tetrahedron Letters,* 1990, 31(50) 7301–7304.
6) Hann, M. M.; Sammes, P. G.; Kennewell, P. D.; Taylor, J. B. *J. Chem. Soc. Perkin I* 1982, 307–311.
7) Hann, M. M.; Sammes, P. G.; Kennewell, P. D.; Taylor, J. B. *J. Chem. Soc. Chem. Comm.* 1980, 234–235.

The available methods all suffer from various shortcomings in stereoselectivity, generality or overall ease of synthesis. The route outlined below was used for the synthesis of the derivatives reported here. This route parallels the route reported by J. Wai et al.

Scheme I

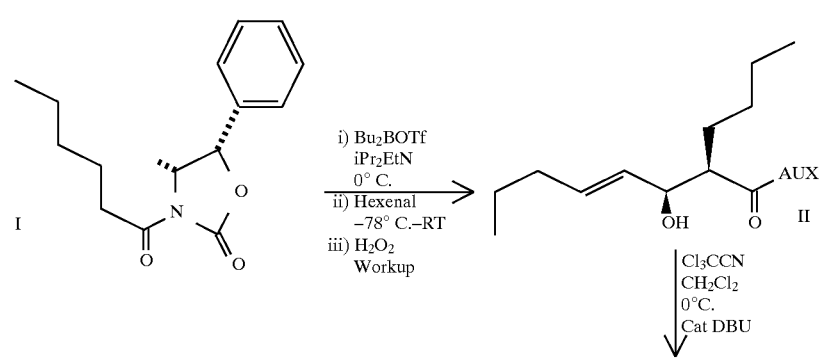

-continued
Scheme I

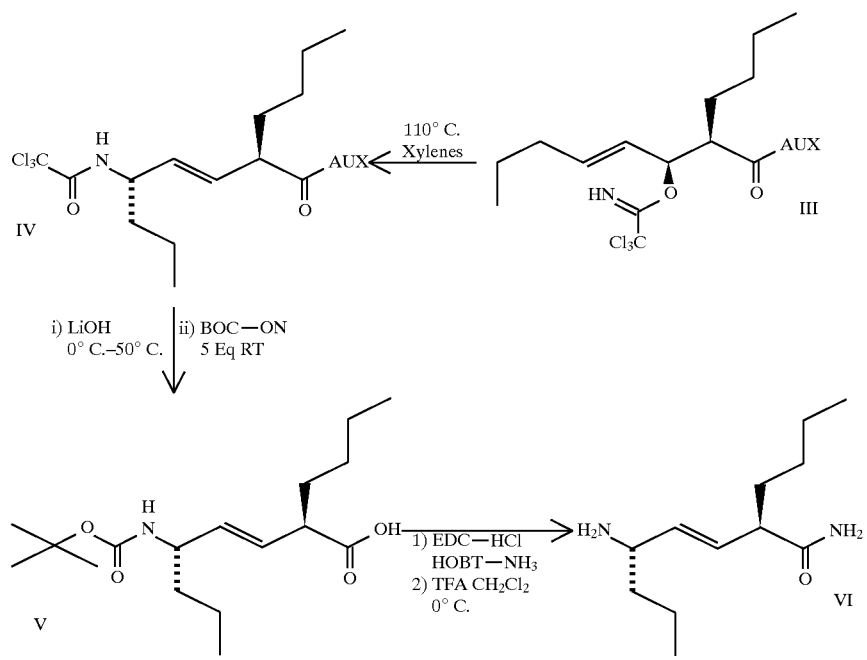

The highly enantiofacially selective aldol type condensation of an imide boron enolate similar to I and an aldehyde by the methods of D. A. Evans et al is very well known and reliable. See (8) and many recent publications by D. A. Evans.

8) Evans, D. A.; McGee, L. R. *J. Am. Chem. Soc.* 1981, 103, 2876–2878.

Conditions listed below and detailed elsewhere lead to excellent diastereoselectivity in the condensation. The stereospecific transposition of the 3-OH center of the aldol adduct II to generate the required 5-NHR centered of the Xaaψ[E,CH=CH]Xaa dipeptide isostere IV is well precedented in other contexts as listed in the references below. This transposition was also used in the above referenced work of Wai et al.

9) Gonda, J.; Helland, A.-C.; Ernst, B.; Bellus, D. *Synthesis* 1993, 729–733.

10) Doherty, A. M.; Kornberg, B. E.; Reily, M. D. *J. Org. Chem.* 1993, 58, 795–798.

11) Metz, P.; Mues, C.; Schoop, A. *Tetrahedron,* 1992, 48, 1071–1080.

12) Overman, L. E. *Acc. Chem. Res.* 1980, 13, 218.

13) Overman, L. E. *J. Am. Chem. Soc.* 1976, 98, 2901.

Removal of the chiral auxiliary and the trichloroacetamide residue is unremarkable, with reprotection of the amine residue in situ. The protected N—BOC—Xaaψ[E,CH=CH] Xaa-OH dipeptide isostere V unit is isolated in good overall yield.

One potential shortcoming common to the class of olefin isosteres represented by the unit V is the possible migration of the γ,δ-olefin to the more thermodynamically favored, conjugated, α,β position. A second major focus of this invention is therefore the further elaboration of the Xaaψ [E,CH=CH]Xaa dipeptide isostere to a novel Xaaψ[cPr, trans]Xaa dipeptide isostere as shown below in Scheme II.

In this case the rigid trans amide bond mimic function is performed by the trans cyclopropyl ring of VII. Cyclopropanation of an unconjugated olefin can be achieved by several methods reported in the literature. Some of these methods rely on carbenoid addition to olefins, which allows use of the intermediates already described. See for examples;

14) Smith, P. A. S. Organic Reactions Vol 20 1–131.

15) LeGoff, E. *J. Org. Chem.* 1964, 29, 2048–2049.

Scheme II

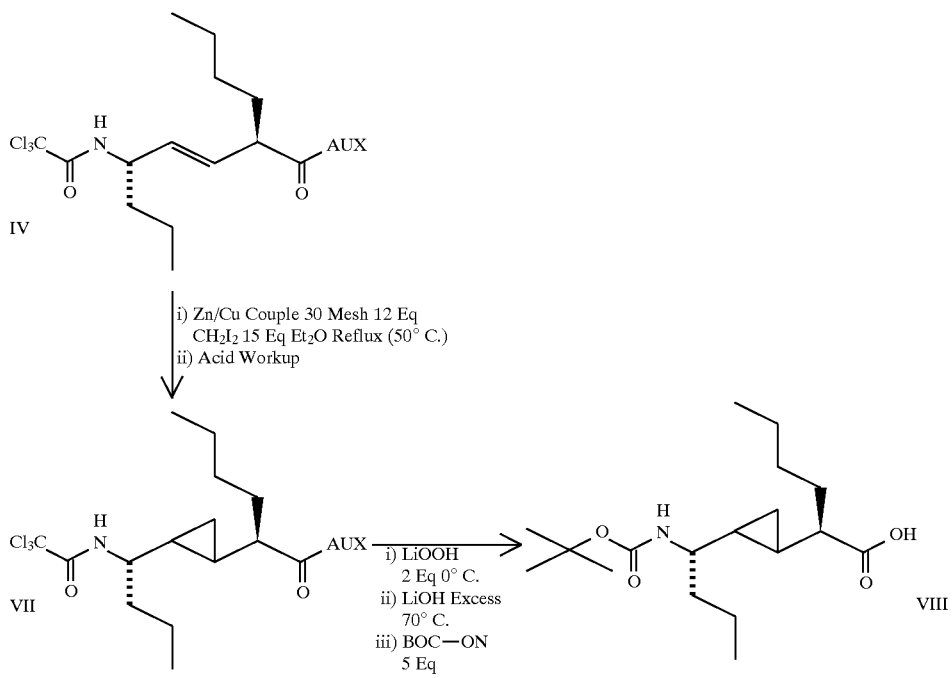

16) Martin S. F.; Oalmann, C. J.; Liras, S. *Tetrahedron* 1993, 49(17) 3521–3532.
17) Kurokawa, N.; Ohfune, Y. *Tet. Let.* 1985, 26(1), 83–84.

For analogs poorly suited to this strategy, the ring may be constructed by ring closure from unrelated intermediates by methods known in the literature. See ref. (18) for an example of this strategy.

18) Burgess, K.; Ho, K.-K.; Ke, C.-Y. *J. Org. Chem.* 1993, 58, 3767–3768. and ref. cited.

The preferred method in this case allows the direct elaboration of the $Cl_3CCO$-Xaaψ[E,CH=CH]Xaa-AUX dipeptide isostere unit IV via a Simmons-Smith cyclopropanation to the desired product in reasonable yield, as a single isomer.

In general either or both of the isomers of the trans cyclopropane unit could be useful as an amide bond geometry mimic, depending on the exact nature of the binding site involved.

Conversion of either the Xaaψ[E,CH=CH]Xaa dipeptide or the Xaaψ[cPr,trans]Xaa isosteres to the complete tetrapeptide register isostere is accomplished by modification of the carboxy function as desired, and appropriate coupling chemistry at the amino terminus with protection and deprotection of functional groups as required.

Conventional carbodiimide/HOBT coupling of the deprotected Xaaψ[E,CH=CH]Xaa or Xaaψ[cPr,trans]Xaa dipeptide isostere and the desired natural or unnatural amino acid, or desired dipeptide fragment leads to completed tetrapeptide register analogs after removal of protecting groups as required. Basic residues in the sidechains of these amino acid or dipeptide fragments are typically BOC protected. See ref. (19) for relevant chemistry.

19) Bodanszky, M.; Bodanszky, A. *The Practice of Peptide Synthesis*, Springer Verlag, Berlin & New York, 1984.

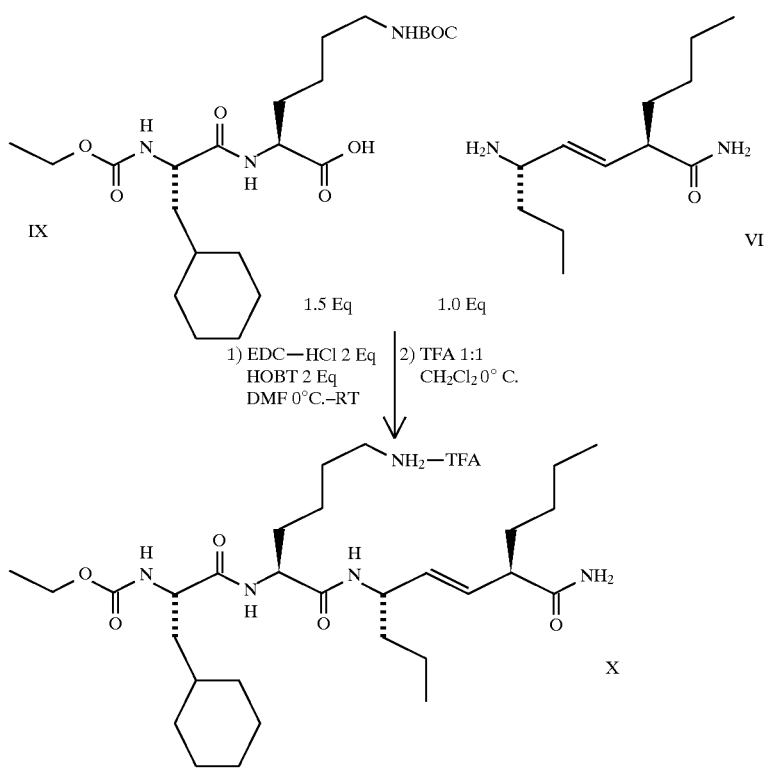

Some of the analogs dealt with here incorporate simple N-alkyl residues in the position corresponding to the P1 position of the tetrapeptide.

Alkylation of a secondary amine is most readily accomplished by the procedure shown in Scheme IV below.

Reductive alkylation of the alpha deprotected tripeptide unit using sodium cyanoborohydride in the presence of an aldehyde or ketone in acidic methanol leads to good yields of the desired monoalkylation product with typically less than 10% of the dialkyl material.

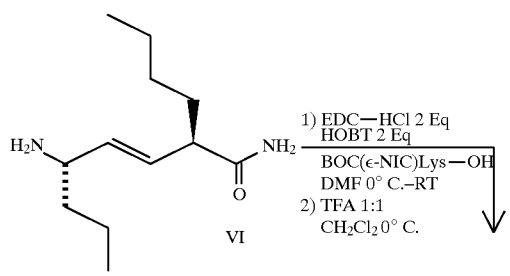

-continued
Scheme III

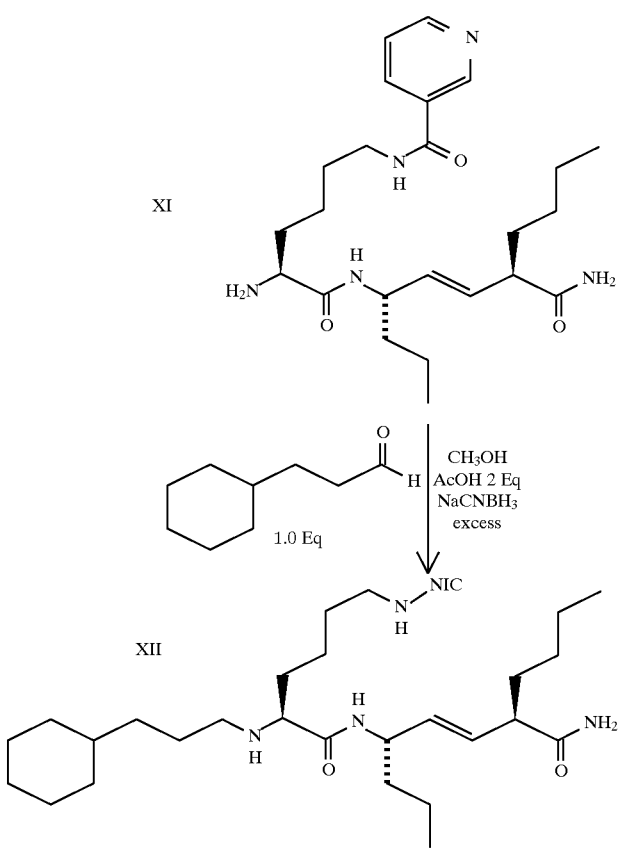

This reductive alkylation is a well known procedure, see; 19) Borch, R. F.; Bernstein, M. D.; Durst, H. D. *J. Am Chem. Soc.* 1971, 93, 2897–2904.

The following examples are not intended to be limitations on the scope of the instant invention in any way, and they should not be so construed. Furthermore, the compounds described in the following examples are not to be construed as forming the only genus that is considered as the invention, and any combination of the compounds or their moieties may itself form a genus. Those skilled in the art will readily understand that known variations of the conditions and processes of the following preparative procedures can be used to prepare these compounds.

General Methods

All temperatures given in the following examples are in degrees Celsius. $^1$H nuclear magnetic resonance (NMR) spectra were recorded at 300, 400 or 500 MHz at ambient temperature in the solvent indicated. Shifts are reported in ppm, referenced to solvent D. Except where indicated, commercially available compounds were used without further purification. All natural and unnatural amino acids are of the (L) configuration unless otherwise noted. Various protected di- and tripeptides were prepared by conventional 1-(3-dimethylaminopropyl)-3-ethylcarbodiimide (EDC)/1-N-Hydroxybenztriazole (HOBT) solution phase couplings of appropriately protected amino acids. Anhydrous solvents were purchased from Aldrich. $CH_2Cl_2$ was, in some cases, distilled from $CaH_2$ before use. All reactions run under anhydrous conditions were run under positive pressure of dry nitrogen.

Abbreviations used are as follows: Cha is cyclohexylalanine, Nva is norvaline, Nle is norleucine, NMP is N-methylpyrollidine, HOBT is hydroxybenzotriazole, DIEA is diisopropylethylamine, TFA is trifluoroacetic acid, Fmoc is 9-fluorenylmethyloxycarbonyl, BOC-ON is [2-(tert-butoxycarbonyloxyimino)-2-phenylacetonitrile, DMF is dimethyl formamide, THF is tetrahydrofuran, EDC is 1-(3-dimethylaminopropyl)-3-ethyl carbodimide, HPLC is high pressure liquid chromatography, RP—HPLC is reversed phase high pressure liquid chromatography, ESI is electrospray ionization, FAB is fast atom bombardment, CS is chemical ionization. TLC is $SiO_2$ thin layer chromatography.

EXAMPLE 1

Nvaψ[E,CH=CH]Nle

Step 1

Preparation of 1-HEXANOYL-(5R)-METHYL-(4S)-PHENYLOXAZOLIDIN-2-ONE

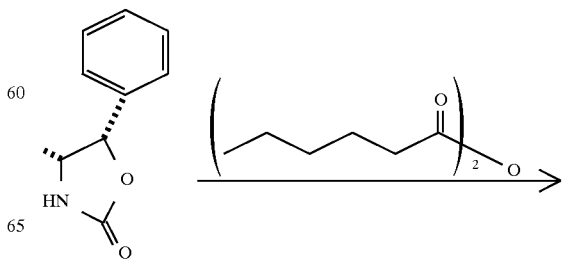

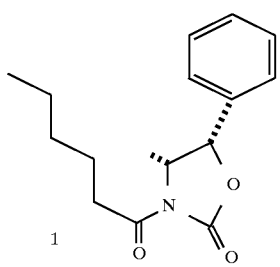

The oxazolidinone (1.0 Eq, 0.02 mol, 3.54 g) was dissolved in THF (20 mL) with Hexanoic anhydride (1.2 Eq, 0.024 mol, 5.6 ml) and LiCl (1.2 Eq, 0.024 mol, 1.02 g). The reaction mixture gelled with a mild exotherm when neat triethyl amine (1.2 Eq, 0.024 mol, 3.55 mL) was added. The mixture was heated at reflux for 16 h to consumption of the oxazolidinone. The reaction mixture was diluted EtOAc/ $H_2O$ and extracted four times with EtOAc. The organic phase was washed with 2N HCl, satd. aq. sodium bicarbonate and brine. The organic phase was dried over $Na_2SO_4$ and reduced i. vac. The crude acylated product was purified by chromatography on $SiO_2$ (40–63μ, 200 g), eluting with 8% EtOAc in hexanes. The product was recovered as an amorphous solid from an oil. MS ESI 80% AcCN/0.1% Aq TFA. Characteristic NMR Resonances; $^1H$ NMR 400 MHz ($CD_3OD$) 7.45–7.34 (m, 5H), 5.77 (d, 1H, J=7.5 Hz), 4.79 (p, 1H, J=6.6 Hz), 2.92 (2H, overlapping ABX systems.), 0.83 (d, 3H, J=6.6 Hz).

Step 2

Preparation of 1-[trans-(2R)-n-BUTYL-(3S)-HYDROXYOCT-4-ENOYL]-(5R)-METHYL-(4S)-PHENYLOXAZOLIDIN-2-ONE

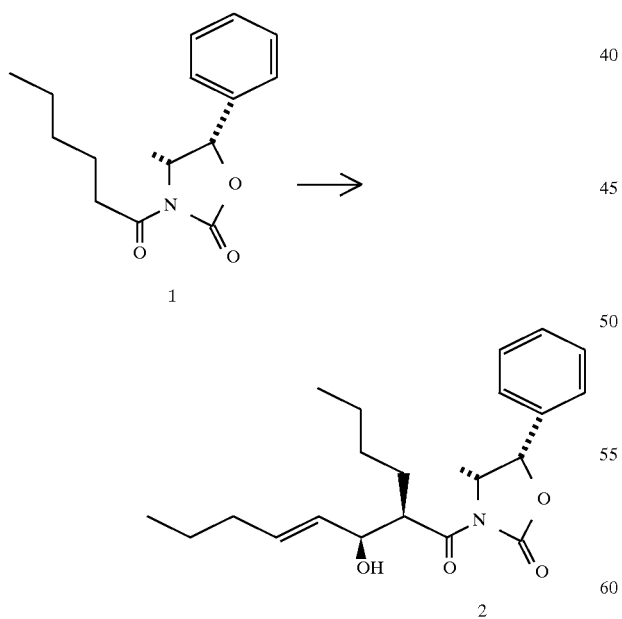

Oxygen was scrupulously excluded in the formation and transfer of the dibutylboron triflate and in the formation of the boron enolates of the acyl oxazolidinones to achieve diastereoselectivity in the following condensations.

Part 1

Dibutylboron Triflate

Dibutylboron triflate was generated in situ and used immediately. Tributylboron (1.0 Eq, 20 mmol, 4.88 mL) was dissolved in $CH_2Cl_2$ (20 mL, Distilled from $CaH_2$ under $N_2$.) in a flask marked for 20 mL volume. Neat trifluoromethanesulfonic acid (1.0 Eq, 20 mmol, 1.77 mL) was added dropwise at a rate allowing controllable exotherm and gas evolution. Stirring was continued for 2 h at RT. Volume was made up to 20 mL with $CH_2Cl_2$.

Part 2

General Condensation Procedure

The imide (1.0 Eq, 17.5 mmol, 4.81 g product of Step 1) was dissolved in $CH_2Cl_2$ (10 mL, distilled) under $N_2$ at 0° C. The 1M $nBu_2BOTf$ solution described above (1.1 Eq, 19.2 mmol, 19.2 mL) was added, followed by neat $iPr_2EtN$ (1.1 Eq, 19.2 mmol, 3.33 mL). The resulting pale yellow solution was stirred at 0° C. 45 minutes, and cooled to −78° C. 2-Hexenal (1.1 Eq, 19.2 mmol, 2.23 mL) was added neat at −78° C., maintained at −78° C. 30 minutes and allowed to warm to RT. The mixture was poured into 250 mL pH 7 phosphate buffer and stirred 1 hour. Phases were separated and the aqueous phase extracted twice with $CH_2Cl_2$. The combined organic phases were dried over $Na_2SO_4$ and reduced i. vac.

The crude product was redissolved in $CH_3OH$ (~100 mL) and cooled to 0° C. Aqueous hydrogen peroxide (~5 mL, nominal 30%) was added and the mixture allowed to stand 1¾ h at 0° C. The mixture was reduced i. vac. and diluted with $CH_2Cl_2$ and $H_2O$. The organic phase was separated and washed with dil. aqueous bisulfite followed by saturated aqueous $NH_4Cl$. The combined organic phases were dried and reduced i. vac.

The crude product was purified by chromatography on $SiO_2$ (40–63μ, 360 g) eluting with 60:40 hexanes:diethyl ether. The product was recovered as an oil. Characteristic NMR Resonances; $^1H$ NMR 400 MHz ($CD_3OD$); 7.4 (M, 5H), 5.67 (d, 1H), 5.59 (2H, AB of ABXY, Partially obscured, JAB=13.2 Hz, JAX=6.5 Hz, JBY=5.9 Hz with fine splitting), 4.14 (m, 2H), 2.04 (q, 2H, J=6.6 Hz), 1.72 (m, 2H), 0.93 (t, 3H, J=7.4 Hz), 0.88 (brd t, 3H, butyl residue), 0.84 (d, 3H, J=6.6 Hz). MS ESI 80% AcCN/0.1% Aq TFA.

Step 3

Preparation of 1[trans-(2R)-n-BUTYL-(5S)-TRICHLOROACETYLAMINOOCT-3-ENOYL]-(5R)-METHYL-(4S)-PHENYLOXAZOLIDIN-2-ONE

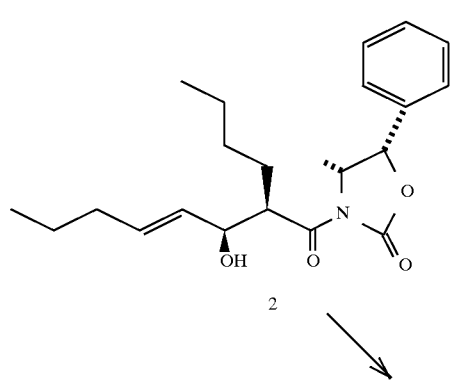

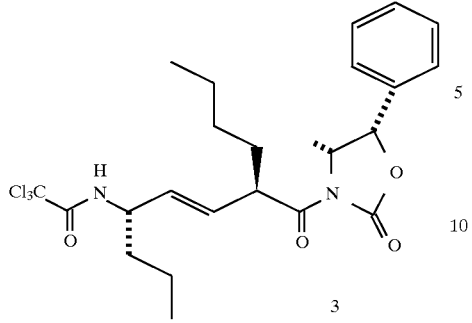

3

General Procedure for Overman Rearrangement

The condensation product of Example 1, Step 2, Part 2 (1.0 Eq, 0.01 mole, 5.1 g) was dissolved in a two to one mixture of $CH_2Cl_2$ (50 mL) and trichloroacetonitrile (25 mL) and cooled to 0° C. Periodic additions of 0.1 Eq DBU (0.2–0.3 Eq, 2–3 mmol, 300–450 mL) were made while stirring at 0° C. until the starting hydroxy compound was consumed as indicated by analytical TLC. Typically two or three additions at one hour intervals were necessary. The reaction mixture was reduced i. vac. and purified by $SiO_2$ chromatography (40–63µ, 180 g) eluting with 9% ethyl acetate in hexanes. The intermediate was unstable, and was not characterized in all cases.

The product from the above was dissolved in xylene (125 mL), degassed by nitrogen versus vacuum purge, and heated to 140° C. for 2¼ h. The solution was cooled to RT and loaded on a $SiO_2$ column (40–63µ, 200 g) which had been packed in straight hexanes. Xylenes were eluted off with 200 mL hexanes and the product eluted with 15% ethyl acetate in hexanes. The product was recovered as an oil. MS ESI 80% AcCN/0.1% Aq TFA. Characteristic NMR Resonances; $^1H$ NMR 400 MHz ($CD_3OD$); 7.4 (m, 5H), 5.75 (d, 2H, J=7.1 Hz), 5.68 (2H, AB of ABXY, Partially obscured, JAB=15.5 Hz, JAX=9.0 Hz with fine splitting, JBY=6.8 Hz), 4.39 (m, 1H, six lines), 4.34 (q, 1H, J=8.4 Hz, unresolved fine splitting), 0.94 (t, 3H, J=7.3 Hz), 0.88 (brd. t, 3H, butyl residue), 0.84 (d, 3H, J=6.6 Hz).

Step 4

Preparation trans-(2R)-n-BUTYL-(5S)-(t-BUTOXYCARBONYLAMINO)OCT-3-ENOIC ACID, BOC—Nvaψ[E,CH=CH]Nle-OH

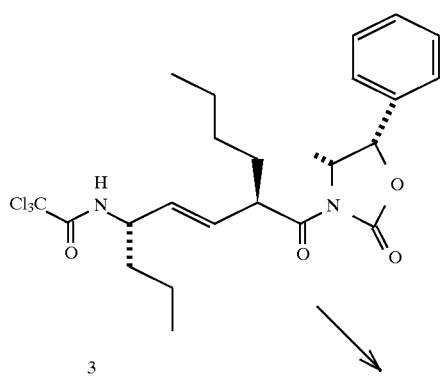

3

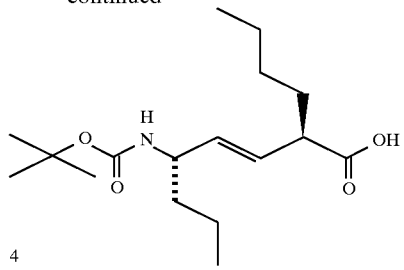

4

The imide (product of Example 1, Step 3) 1.0 Eq, 2.26 mmol, 1.2 g) was dissolved in THF (20 mL) and cooled to 0° C. Aqueous 2M LiOH (6.0 Eq, 13.6 mmol, 6.8 mL) was dropped in. The mixture was stirred at 0° C. until the cleavage of the imide residue was complete as judged by TLC. The mixture was allowed to warm to RT and subsequently heated overnight at 55° C. (16 h at 55° C.). The mixture was cooled to RT and BOC—ON (5.0 Eq, 11.3 mmol, 2.8 g) was added. The mixture was stirred at RT for 24 h. The reaction mixture was diluted with EtOAc and dil. aq. sodium bicarbonate and the aqueous phase washed 4 times with EtOAc. The organic phase from this wash was discarded. The aqueous phase was acidified to pH ~2, and extracted with EtOAc. The organic phase from the acidic extraction was dried over $Na_2SO_4$ and reduced i. vac. The crude acid was obtained as an oil sufficiently pure for further conversion. MS ESI 80% AcCN/0.1% Aq TFA. Characteristic NMR Resonances; $^1H$ NMR 400 MHz ($CD_3OD$); 5.68 (2H, AB of ABXY, Δδ=39.7 Hz, JAB=15.4 Hz, JAX=8.4 Hz, JBY=6.5 Hz), 3.94 (brd q, 1H), 2.91 (q, 1H, J=8.2 Hz), 1.7 (m, 1H), 0.91 (t, 3H, J=7.3 Hz), 0.89 (t, 3H, J=7 Hz).

Step 5

Preparation of trans-(2R)-n-BUTYL-(5S)-(t-BUTOXYCARBONYLAMINO)OCT-3-ENOYL AMIDE BOC-Nvaψ[E,CH=CH]Nle-NH₂

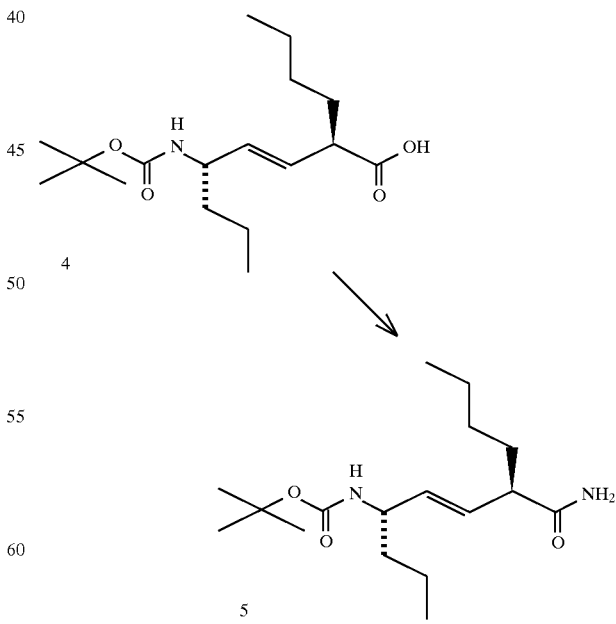

The free acid (product of Example 1, Step 4, 1.0 Eq, 0.53 mmol, 166 mg) was dissolved in DMF (anhydr. 2.5 mL) with HOBT—$NH_3$ (2.0 Eq, 1.06 mmol, 161 mg) and EDC—

HCl (2.0 Eq, 1.06 mmol, 203 mg) was added at 0° C. The mixture was stirred overnight at 0° C. and then allowed to come to RT for ½ hour. The reaction mixture was poured into H₂O and extracted with EtOAc. The EtOAc phase was washed with H₂O, washed with brine, dried over Na₂SO₄ and reduced i. vac. The crude mixture was purified by elution from a 25×700 mm Sephadex LH-20-100 column with CH₃OH. The product was obtained as an amorphous solid. MS ESI 80% AcCN/0.1% Aq TFA; 313.1, M+1 for calculated 312.24, 625.5 dimer+1. Characteristic NMR Resonances; ¹H NMR 400 MHz (CD₃OD); 5.52 (2H, AB of ABXY, Δδ=32.5 Hz, JAB=15.8 Hz, JAX=8.3 Hz, JBY=6.1 Hz), 3.94 (brd q, 1H), 2.87 (q, 1H, J=7.7 Hz), 1.7 (m, 1H), 1.42 (s, 9H), 0.91 (t, 3H, J=7.2 Hz), 0.89 (t, 3H, J=7 Hz).

Step 6

Preparation of trans-(2R)-n-BUTYL-(5S)-AMINOOCT-3-ENOYL AMIDE TRIFLUOROACETATE SALT. TFA Nvaψ[E, CH=CH]Nle-NH₂

Typical BOC Removal Procedure

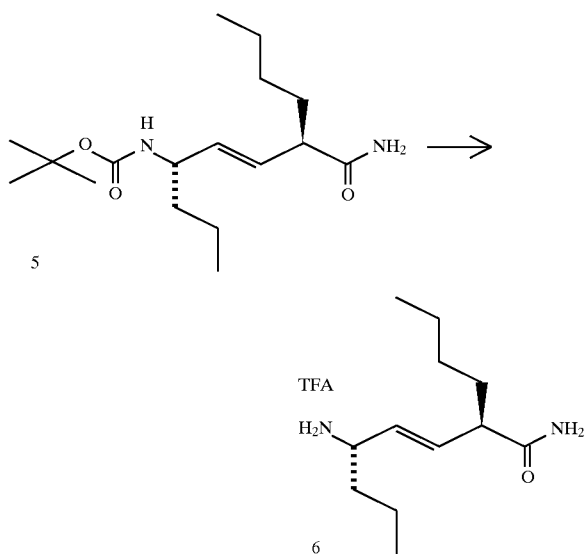

The BOC amino amide product of Example 1, Step 5, was dissolved/suspended in CH₂Cl₂ and cooled to 0° C. An equal volume of trifluoroacetic acid was dropped in, and the solution stirred at 0° C. for 1 Hr. The mixture was reduced i. vac. and excess TFA removed immediately by elution from a 12.5×700 mm Sephadex LH-20-100 column with CH₃OH and reduction of fractions i. vac. The product was obtained as an amorphous solid. MS ESI 80% AcCN/0.1% Aq TFA. Characteristic NMR Resonances; ¹H NMR 400 MHz (CD₃OD); 5.58 (2H, AB of ABXY, Δδ=139.9 Hz, JAB=15.8 Hz, JAX=7.9 Hz, JBY=8.3 Hz), 3.66 (m, 1H), 2.87 (q, 1H, J=7.5 Hz), 0.95 (t, 3H, J=7.3 Hz), 0.91 (t, 3H, J=6.9 Hz).

EXAMPLE 2

Nvaψ[E,CH=CH]Leu

Step 1

Preparation of 1-[4-METHYLPENTANOYL]-(5R)-METHYL-(4S)-PHENYLOXAZOLIDIN-2-ONE

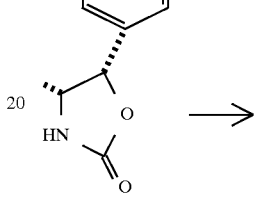

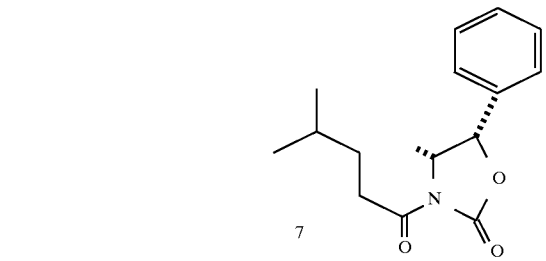

The acyl oxazolidinone was prepared from (5R)-methyl-(4S)-Phenyl-oxazolidinone (5 g) as for Example 1, Step 1. The product was obtained as a waxy solid. Characteristic NMR Resonances; ¹H NMR 400 MHz (CD₃OD); 7.35–7.45 (m, 5H), 5.77 (d, 1H, J=7.4 Hz), 4.79 (p, 1H, J=6.6 Hz), 2.93 (2H, overlapping ABX systems.), 0.94 (d, 6H, J=6.4 Hz), 0.83 (d, 3H, J=6.6 Hz).

Step 2

Preparation of 1-[trans-(2R)-[2-METHYL-PROPYL]-(3S)-HYDROXYOCT-4-ENOYL]-(5R)-METHYL-(4S)-PHENYLOXAZOLIDIN-2-ONE

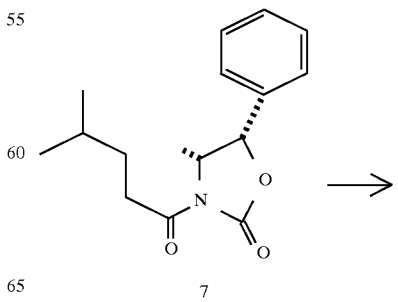

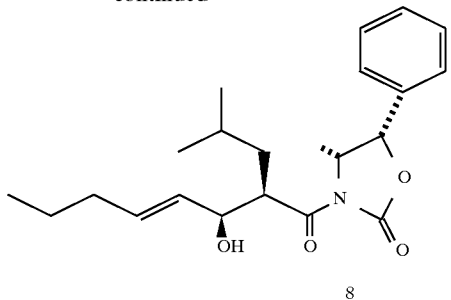

8

The aldol type condensation of the imide (2.5 g product of Step 1, Example 2) was run as per the general procedure of Example 1, Step 2 above. The product was obtained as an oil. Characteristic NMR Resonances; $^1$H NMR 400 MHz (CD$_3$OD); 7.4 (m, 5H), 5.67 (d, 1H, J=7.1 Hz), 5.59 (2H, AB of ABXY, partially obscured, JAB=15.4 Hz, JBY=6.23 Hz with fine splitting), 4.79 (pent, 1H, J=6.6 Hz), 4.29 (m, 1H), 4.08 (t, 1H, J=7 Hz), 2.04 (q, 2H, J=6.7 Hz), 1.77 (m, 1H), 0.93 (t, 3H, J=7.4 Hz), 0.89 (d, 3H, J=6.1 Hz), 0.89 (d, 3H, 6.1 Hz), 0.83 (d, 3H, J=6.6 Hz).

Step 3

Preparation of 1[trans-(2R)-[2-METHYLPROPYL]-(5S)-TRICHLOROACETYLAMINOOCT-3-ENOYL]-(5R)-METHYL-(4S)-PHENYLOXAZOLIDIN-2-ONE

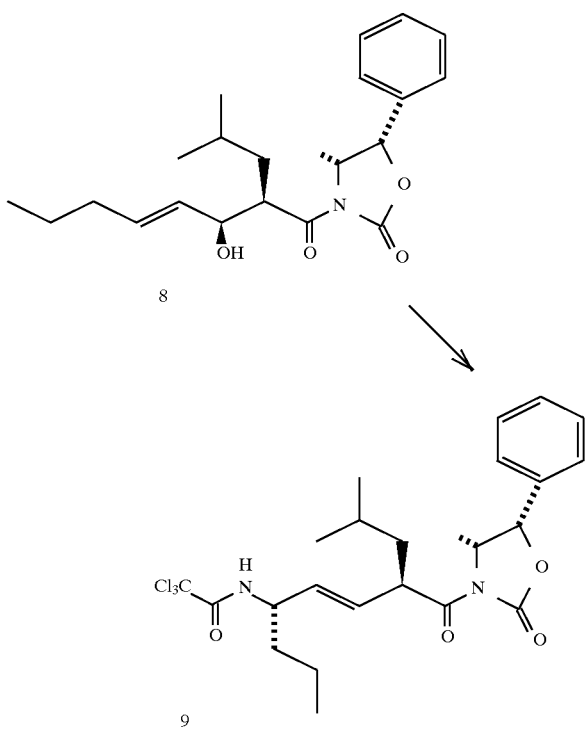

The trichloroacetimidate intermediate was prepared from the aldol condensation product (1.18 g product of Example 2, Step 2) as per the general procedure of Example 1, Step 3. The product was obtained as an oil. Characteristic NMR Resonances; $^1$H NMR 400 MHz (CD$_3$OD); 7.4 (m, 5H), 5.86 (dt, 1H, J=14.4, 7.0), 5.71 (d, 1H, J=7.3), 5.57 (m, 1H), 4.81 (pent, 1H, J=7 Hz), 4.57 (m, 1H, 10 lines), 2.07 (q, 2H, J=6.9 Hz), 1.86 (m, 1H), 0.91 (m, 9H, methyl resonances overlap 4 sharp lines.), 0.85 (d, 3H, J=6.6 Hz).

The purified trichloroacetimidate intermediate (1.0 Eq, 3.87 mmol, 2.0 g) was rearranged as per the general procedure of Example 1, Step 3 above. The product was recovered as an oil. Characteristic NMR Resonances; $^1$H NMR 400 MHz (CD$_3$OD); 7.4 (m, 5H), 5.75 (d, 1H, J=7.4 Hz), 5.67 (2H, AB of ABXY partially collapsed, Δδ small, JAB=15.5, JAX=7.4, JBY=6.3), 4.78 (pent, 1H, J=7 Hz), 4.57 (m, 1H, q with fine splitting), 4.30 (m, 1H, q with fine splitting), 0.94 (t, 3H, J=7.4 Hz), 0.906 (d, 1H, J=6.4 Hz), 0.899 (t, 3H, J=6.4 Hz), 0.83 (d, 3H, J=6.6 Hz).

Step 4

Preparation of trans-(2R)-[2-METHYLPROPYL]-(5S)-(t-BUTOXYCARBONYLAMINO)OCT-3-ENOIC ACID, BOC-Nvaψ[E,CH═CH]Leu-OH

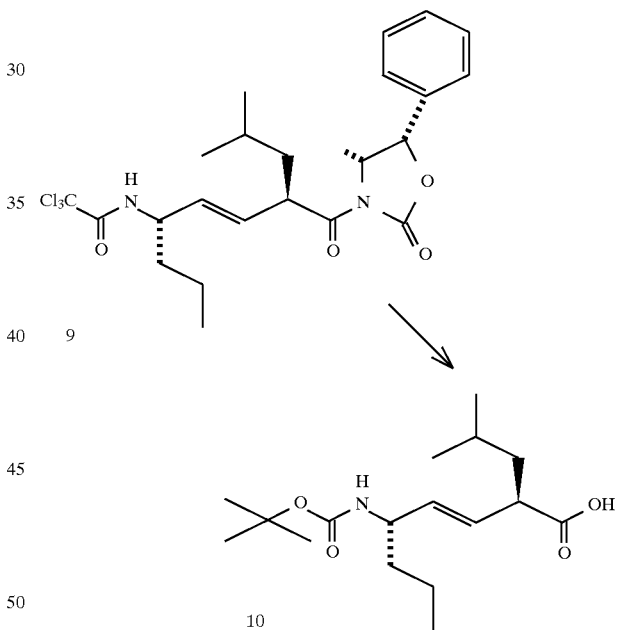

The conversion to the BOC—Nvaψ[CH═CH,trans]Leu-OH was run as per the general procedure of Example 1, Step 4 above. Characteristic NMR Resonances; $^1$H NMR 400 MHz (CD$_3$OD); 5.68 (2H, AB of ABXY, Δδ=26.9 Hz, JAB=15.4 Hz, JAX=8.4 Hz, JBY=6.2 Hz), 3.92 (brd q, 1H), 3.02 (q, 1H, J=7.7 Hz), 1.6 (m, 2H), 0.91 (t, 3H, J=7.3 Hz), 0.90 (d, 3H, J=6.3 Hz), 0.87 (d, 3H, J=6.2 Hz).

Step 5

Preparation of trans-(2R)-[2-METHYLPROPYL]-(5S)-(t-BUTOXYCARBONYLAMINO)OCT-3-ENOYL AMIDE. BOC-Nvaψ[E,CH=CH]Leu-NH₂

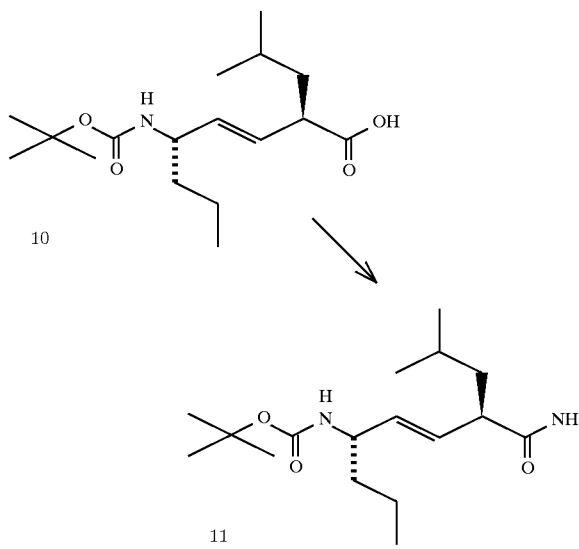

The amide (11) was prepared from the acid (103 mg product of Example 2, Step 4) as per the general procedure of Example 1, Step 5. Characteristic NMR Resonances; ¹H NMR 400 MHz (CD₃OD); 5.46 (2H, AB of ABXY system, Δδ=20.9 Hz, JAB=15.6 Hz, JAX=8.0 Hz, JBY=5.5 Hz), 3.88 (brd q, 1H), 3.0 (q, 1H, J=7.5 Hz), 1.57 (m, 2H), 1.37 (s, 9H), 0.91 (6H, two overlapping methyl resonances), 0.87 (d, 3H, J=6.2 Hz).

Step 6

Preparation of trans-(2R)-[2-METHYLPROPYL]-(5S)-AMINOOCT-3-ENOYL AMIDE TRIFLUOROACETATE SALT. TFA Nvaψ[E,CH=CH]Leu-NH₂

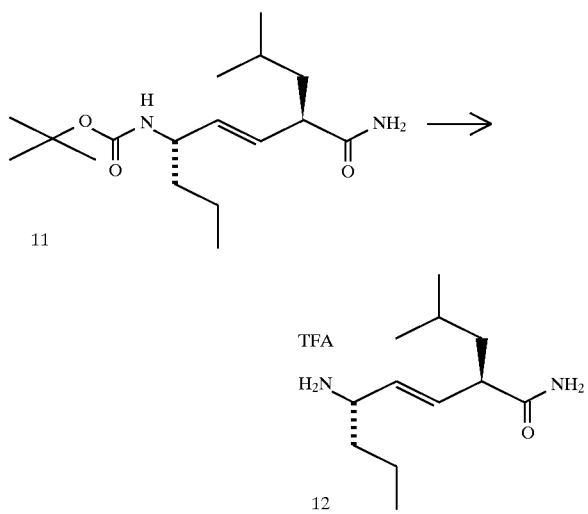

The (α-BOC) amide (50 mg) from Step 5, Example 2 above was deprotected and purified as for the general procedure of Step 6, Example 1 above. The product was recovered as an oil. Characteristic NMR Resonances; ¹H NMR 400 MHz (CD₃OD); 5.69 (2H, AB of ABXY system, Δδ=124 Hz, JAB=15.4 Hz, JAX=8.7 Hz, JBY=8.3 Hz), 3.66 (m, 1H), 3.12 (q, 1H, J=7.6 Hz), 0.95 (t, 3H, J=7.3 Hz), 0.94 (d, 3H, J=6.5 Hz), 0.9 (d, 3H, J=6.4 Hz).

EXAMPLE 3

Nvaψ[cPr,trans]Nle

Step 1

Cyclopropanation of OLEFIN Cl₃CCO—Nvaψ[E,CH=CH]Nle-(5R)-METHYL-(4S)-PHENYLOXAZOLIDIN-2-ONE IMIDE

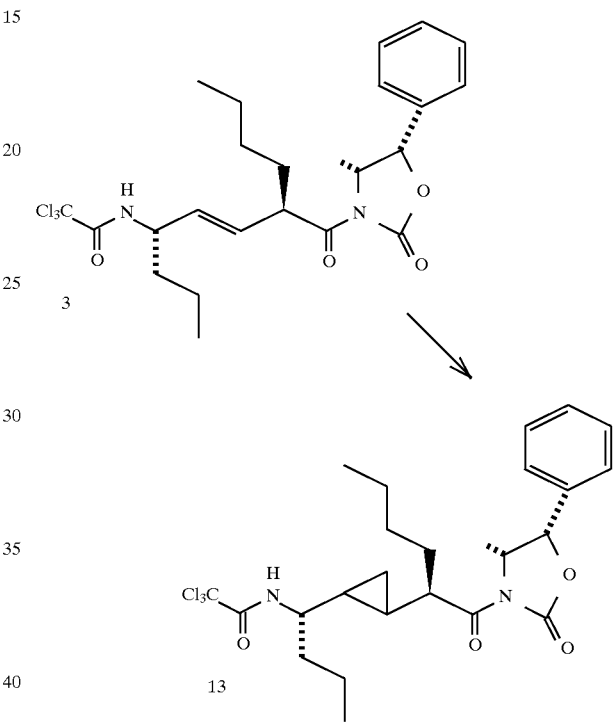

General Cyclopropanation Procedure

Part 1

Preparation of Zn/Cu Couple

The Zn Cu couple used was prepared after Legoff (*J. Org. Chem.* 1964, 29, 2048.). Cupric Acetate (0.5 g) was dissolved in AcOH (50 mL) and heated to 100° C. Granulated Zn (30 g, 30 Mesh) was added in one portion, and heating continued until the cupric acetate was consume as judged by color. The mixture was decanted and washed twice with hot AcOH (~50 mL each), followed by two careful washings with diethyl ether (~50 mL each). A fine red silt is decanted with the AcOH. The brick red solid was dried under a stream of N₂ and stored under N₂. The material shows good reactivity for about one week.

Part 2

Preparation of (13)

The Zn/Cu couple (prepared in Example 3, Step 1, Part 1) 15 Eq, 11.2 mmol, 730 mg) was weighed out in a dried flask and the flask flushed with N₂. Enough ether was added to cover the solid (~300 μL). About 20% of the CH₂I₂ (total 12 Eq, 8.9 mmol, 724 μL was used) and a very small crystal of iodine were added and the mixture heated at reflux for about 20 min. The olefin (1.0 Eq, 0.75 mmol, 387 mg) was dissolved in diethyl ether (700 µL) and four to five equal additions of the olefin and the remaining CH₂I₂ were made over about 1½ h. Reflux was continued until most of the starting material was consumed, approximately an additional 1½ h. The reaction mixture was cooled to RT, diluted with EtOAc and 2N HCl and extracted 4 times EtOAc. The combined EtOAc extracts were washed with dil. aq. sodium bisulfite, dried over Na₂SO₄ and reduced i. vac. The Crude product was purified by chromatography on SiO2 (40–63µ, 20 g), eluting with 12% EtOAc in Hexanes. The desired cyclopropane was recovered as a solid, crystallized from an oil. MS ESI 80% AcCN/0.1% Aq TFA; 531, 533, 535 pattern appropriate for trichloro isotope mixture, M+1's for 530.15 (³⁵Cl₃) calc. Complete ¹H NMR 400 MHz (CD₃OD); 7.38 (m, 5H), 5.78 (d, 1H, J=7.4 Hz), 4.85 (pent, 1H, J=6.6 Hz), 3.28 (partially Obscured by CD30D, dt?, 1H, J=5.1, 9.5), 3.17 (dt, 1H, J=5.1, 9.4 Hz), 1.8 (m, 1H), 1.7 (m, 2H), 1.2–1.45 (m's, 7H), 1.07 (sep, 1H, cPr, J=4.4 Hz), 0.97 (m, 1H, cPr partially obscured), 0.92 (t, 3H, J=7.4), 0.86 (t, 3H, J=7 Hz), 0.83 (d, 3H, J=6.6 Hz), 0.63 (dt, 1H, cPr, J=8.6, 5.1), 0.46 (dt, 1H, cPr, J=8.5, 5.0).

Step 2

Preparation of 2-(1"-tert-BUTOXYCARBONYLAMINOBUTYL)-1-CYCLOPROPANE- 1'-BUTYLACETIC ACID; BOC—Nvaψ[cPr,trans]Nle-OH

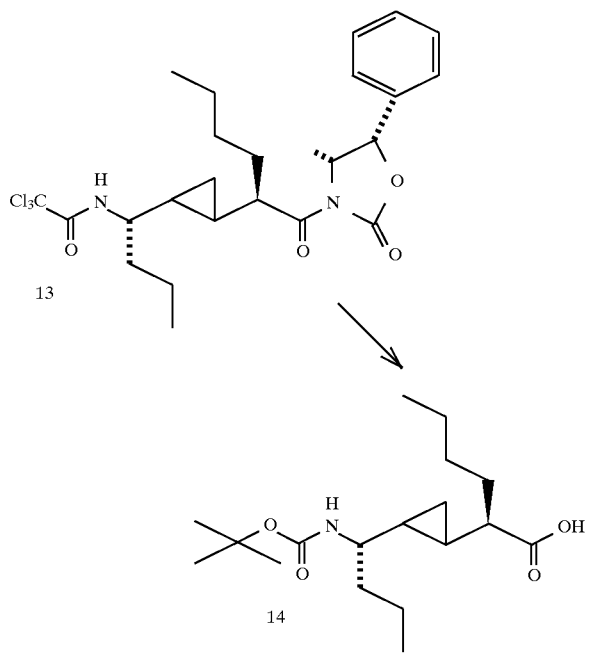

The imide (63 mg, 0.119 mmol, product of Example 3, Step 1) was dissolved in 3:1 THF:H₂O (1.7 mL) and cooled to 0° C. Hydrogen peroxide (4.0 Eq, nominal 30%, 54 µL) was added, followed by 2M LiOH(2.0 Eq, 0.24 mmol, 119 µL). The mixture was stirred at 0° C. until analytical TLC indicated complete cleavage of the imide. A large excess of LiOH (1.6 mL) was added and the mixture was heated at 70° C. for 72 Hrs. The mixture was cooled to RT and BOC—ON (5.0 Eq, 0.59 mmol, 146 mg) was added. THF was added to give a reasonably homogenous mixture. After 24 Hrs at RT, the mixture was diluted with EtOAc and dil aq sodium bicarbonate. The aqueous phase was washed four times with EtOAc and the washes discarded. The aqueous phase was acidified to pH ~2–3 with 2N HCl and extracted with EtOAc. The combined EtOAc extracts were dried over Na₂SO₄ and reduced i. vac. Characteristic NMR Resonances; ¹H NMR 400 MHz (CD₃OD); 2.89 (m, 1H), 1.43 (s, 9H), 0.973 (m, odd number of lines, 1H), 0.899 (t, 6H, J=7.3), 0.645 (sept, 1H), 0.473 (dt, 1H, J=8.5, 5.0), 0.392 (dt, 1H, J=8.5, 5.0).

Step 3

Preparation of 2-((S)1"-AMINOBUTYL) CYCLOPROPANE-1-((R)2'-BUTYLACETAMIDE) TRIFLUOROACETATE TFA—Nvaψ[cPr,trans] Nle-NH₂

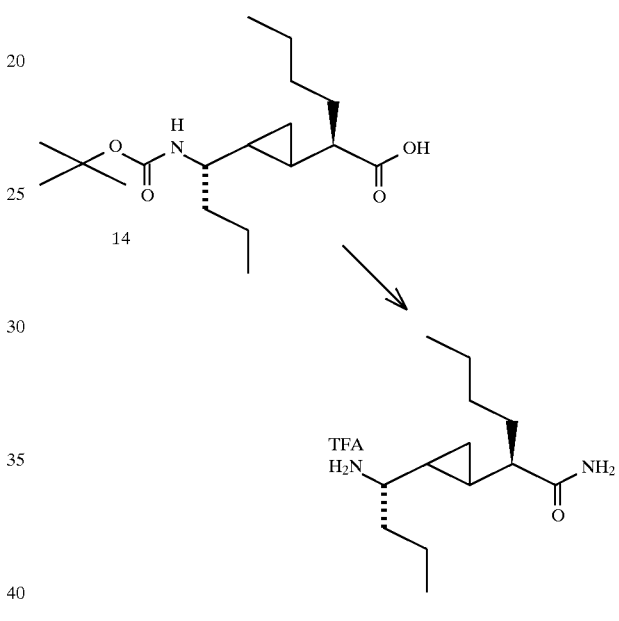

Step 3

Preparation of (α-BOC)-Nvaψ[cPr,trans]Nle-NH₂

The (α-BOC) protected amide was prepared from the (α-BOC) protected acid (8.7 mg, product of Example 3, Step 2) as per the general procedure of example 2, step 5 above. Characteristic NMR Resonances; ¹H NMR 400 MHz (CD₃OD); 2.93 (m, 1H), 1.43 (s, 9H), 0.66 (sept, 1H, J=4.2 Hz), 0.48 (dt, 1H, J=4.9 Hz), 0.37 (dt, 1H, J=5 Hz).

Step 4

Preparation of TFA Nvaψ[cPr,trans]Nle-NH₂

Using the general TFA BOC cleavage procedure of Example 1, Step 6 above; from the (α-BOC) compound of Example 3, step 3 (8.3 mg), the deprotected amino amide intermediate was obtained in essentially quantitative yield.

Characteristic NMR Resonances; ¹H NMR 400 MHz (CD₃OD); 2.51 (q, 1H), 1.02 (m, 1H, partially obscured), 0.975 (t, 3H, J=7.3 Hz), 0.911 (t, 3H, J=7.1 Hz), 0.7–0.8 (overlapping m's, 2H), 0.587 (dt, 1H, J=8.7, 4.2 Hz).

TETRAPEPTIDE MIMICS

EXAMPLE 4

EtOCO—(L)Cha(L)Lys Nvaψ[E,CH=CH]Nle-NH$_2$TFA

5

Step 1

Preparation of EtOCO—(L)Cha (L)(ε-BOC)Lys Nvaψ[E,CH=CH]Nle-NH$_2$

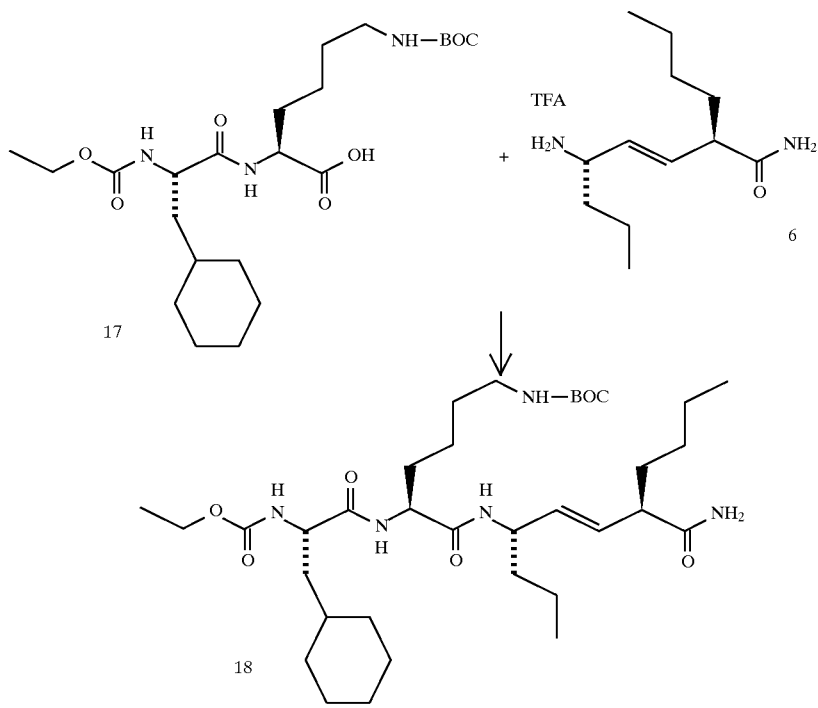

Typical EDC/HOBT Coupling Procedure

Typical amide bond couplings were run with EDC—HCl and HOBT as coupling reagents. The starting acid (1.0–1.25 Eq), HOBT (2.0 Eq) and the amine partner (1.0 Eq) were dissolved in DMF (typically 500 μL for a 20–30 mg of the amine partner) and cooled to 0° C. When a salt of the amine partner was used, iPr$_2$EtN (1.0 Eq) was added. Solid EDC—HCl (2.0 Eq) was added, and the reaction mixture stirred to dissolve the reagents. The mixture was stored overnight at 0° C., and brought to RT for one hour. The mixture was poured into EtOAc/dil. aq. sodium bicarbonate and extracted 4 times EtOAc. The organic phase was washed once with satd. aq. NH$_4$Cl, dried over Na$_2$SO$_4$ and reduced i. vac. Products were purified by elution from a Sephadex LH-20-100 column with CH$_3$OH (RI Detection). Compounds were characterized by MS and 400 MHz $^1$H NMR.

From the coupling of TFA—H—Nvaψ[(E)CH=CH]Nle-NH$_2$ (product of Example 1, Step 6, 19 mg, 0.06 mmol) and EtOCO—Cha (ε-BOC)Lys-OH (27.2 mg, 0.11 mmol, prepared by EDC/HOBT solution phase couplings described previously), as per the general procedure above, the desired tetrapeptide mimic was obtained. Characteristic NMR Resonances; $^1$H NMR 400 MHz (CD$_3$OD); 5.57 (2H, AB of ABXY, Δδ=25 Hz, JAB=13.6 Hz, JAX=8 Hz, JBY=7.8 Hz), 4.3 (m, 2H), 3.0 (brd m, 3H), 2.87 (q, 1H, J=7.8 Hz), 1.42 (s, 9H), 0.89 (t, 3H, J=6.2 Hz).

Step 2

Preparation of EtOCO—(L)Cha (L)Lys Nvaψ[E, CH=CH]Nle-NH$_2$ TFA SALT

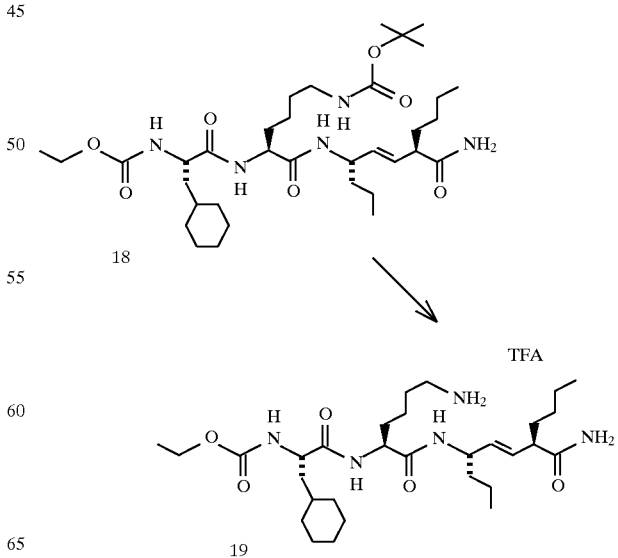

The tetrapeptide mimic was deprotected according to the typical tert-Butoxy carbonyl protecting group removal procedure of Example 1, Step 6. MS ESI 80% AcCN/0.1% Aq TFA 566.3, M+1 for calculated 565.42. Characteristic NMR Resonances; $^1$H NMR 400 MHz (CD$_3$OD); 5.56 (m, 2H, collapsed ABXY system), 4.36 (dd, 1H, J=8.5, 5.9 Hz; overlaps m, 1H), 4.07 (q, 2H, J=7.1 Hz; overlaps m, 1H), 2.92 (t, 2H, J=7.5 Hz; overlaps m, 1H), 1.24 (t, 3H, J=7.1), 0.90 (two overlapping triplets, 6H).

EXAMPLE 5

EtOCO-(L)Cha (L)Lys Nvaψ[(E,CH=CH]Leu-NH$_2$ TFA SALT

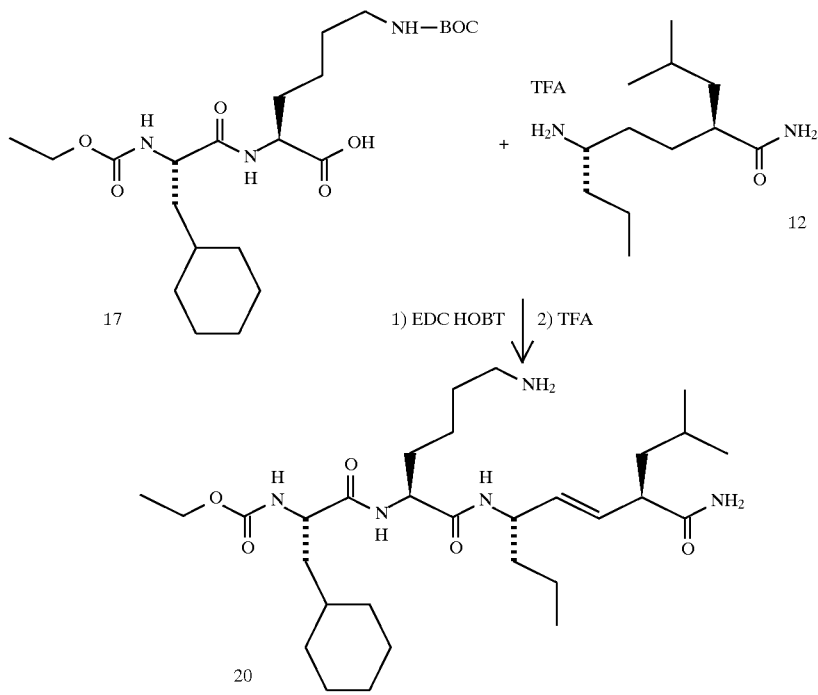

Step 1

Preparation of EtOCO—(L)Cha (α-BOC)(L)Lys Nvaψ[E,CH=CH]Leu-NH$_2$

Using the general EDC/HOBT coupling as for Example 4, Step 1 above; from TFA—Nvaψ[CH=CH,trans]Leu-NH$_2$ (product of Example 2, Step 6, 16 mg, 0.049 mmol) and EtOCO—Cha (ε-BOC)Lys-OH (34.7 mg, 0.074 mmol, prepared by EDC/HOBT solution phase coupling), the desired tetrapeptide mimic was obtained. Characteristic NMR Resonances; $^1$H NMR 400 MHz (CD$_3$OD); 5.54 (2H, collapsed AB pattern), 4.3 (brd m, 2H), 4.1 (brd m, 3H), 3.01 (superposed t & q, 3H), 1.42 (s, 9H), 1.24 (t, 3H, J=7.1 Hz), 0.91 (d, 3H, J=6.3 Hz), 0.9 (t, 3H, J=7.3 Hz), 0.87 (d, 3H, J=6.3 Hz).

Step 2

Preparation of EtOCO-(L)Cha (L)Lys Nvaψ[(E) CH=CH]Leu-NH$_2$

Using the general TFA BOC cleavage as for Example 1, Step 6 above; From the (α-BOC) (28.6 mg) compound, the deprotected tetrapeptide mimic was obtained. MS ESI 80% AcCN/0.1% Aq TFA 566.3, M+1 for calculated 565.4. Characteristic NMR Resonances; $^1$H NMR 400 MHz (CD$_3$OD); 5.55 (2H, collapsed AB pattern), 4.36 (2 superposed m's, 2H), 4.08 (2 superposed m's, 3H), 3.03 (q, 1H, J=7.5 Hz), 2.92 (t, 2H, J=7.6 Hz), 1.24 (t, 3H, J=7.1 Hz), 0.92 (d, 3H, J=6.3 Hz), 0.9 (t, 3H, J=7.3 Hz), 0.88 (d, 3H, J=6.3 Hz).

EXAMPLE 6
EtOCO-(L)Cha (L)Lys Nvaψ[trans,cPr]Nle-NH₂
TFA SALT

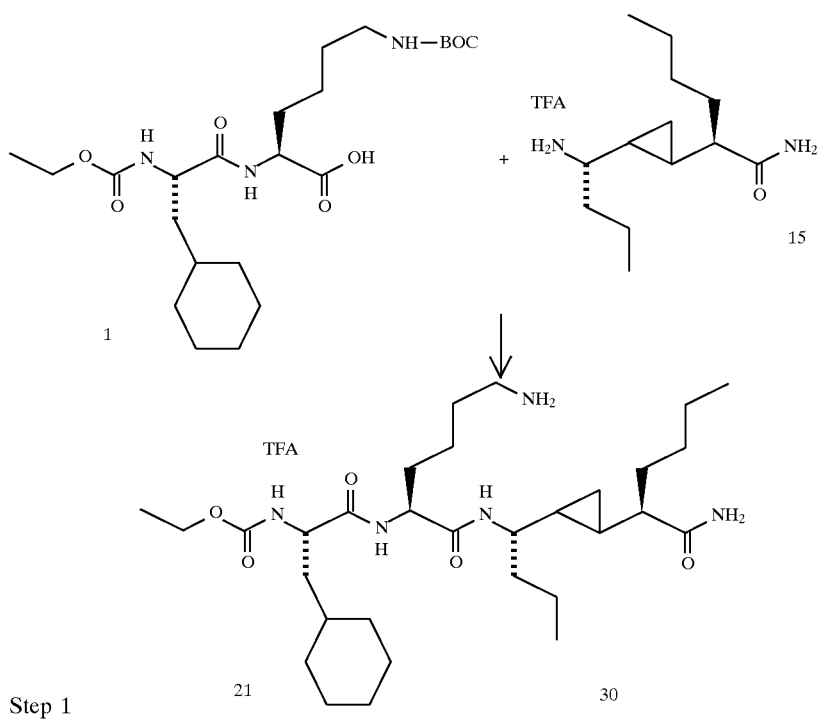

Step 1

Preparation of EtOCO-(L)Cha (α-BOC)(L)Lys Nvaψ[trans cPr]Nle-NH₂

Using the general EDC/HOBT coupling as for Example 4, Step 1; from TFA-Nvaψ[trans,cPr]Nle-NH₂ (8.0 mg, 0.024 mmol) and EtOCO—Cha (ε-BOC)Lys-OH (mg, 0.035 mmol). The coupling product was purified by chromatography on SiO2 eluting with 8:1:1 toluene:EtOAc:iPrOH. The desired tetrapeptide mimic was obtained as an amorphous solid (7.0 mg, 44% of the theoretical yield). Characteristic NMR Resonances; ¹H NMR 400 MHz (CD₃OD); 4.31 (dd, 1H, J=9.5, 4.8 Hz), 4.06–4.15 (overlapping m's, 3H), 3.02 (brd t, 2H, J=5.6 Hz), 1.42 (s, 9H), 1.24 (t, 3H, J=7.1 Hz), 0.90 (t, 3H, J=7.0 Hz), 0.88 (t, 3H, J=7.3 Hz), 0.71 (m, 1H), 0.51 (dt, 1H, J=8.7, 5.0 Hz), 0.39 (dt, 1H, J=8.4, 5.0 Hz).

Step 2

EtOCO-(L)Cha (L)Lys Nvaψ[trans,cPr]Nle-NH₂

Using the general TFA BOC cleavage as for Example 1, Step 6 above, from the (α-BOC) (4.8 mg, product of Step 1) compound, the deprotected tetrapeptide mimic (21) was obtained. MS ESI 80% AcCN/0.1% Aq TFA m/z=580.4, 290.6, (M+1)⁺ and (M+1)⁺⁺ for calculated 579.4. Characteristic NMR Resonances; ¹H NMR 400 MHz (CD₃OD); 4.31 (m, 1H), 4–4.15 (overlapping m's, 3H), 3.02 (t, 2H, J=7.5 Hz), 1.24 (t, 3H, J=7.1 Hz), 0.91 (t, 3H, J=7.1 Hz), 0.89 (t, 3H, J=7.5 Hz), 0.72 (m, 1H), 0.527 (dt, 1H, J=8.6, 5.0 Hz), 0.396 (dt, 1H, J=8.4, 4.9 Hz).

EXAMPLE 7
N-(3-CYCLOHEXYLPROPYL)-(L)(ε-NICOTINOYL)Lys Nvaψ[E,CH=CH]Nle-NH₂
TFA SALT

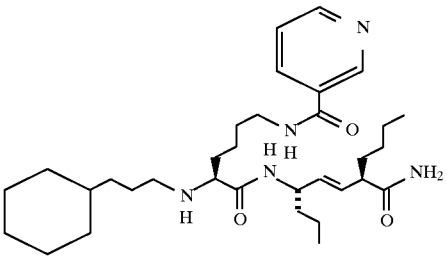

Step 1

Preparation of (α-BOC)(ε-Nicotinoyl)(L)Lys Nvaψ [E,CH=CH]Nle-NH₂

Using the general EDC/HOBT coupling as for Example 4, Step 1 above; the Nvaψ[(E)CH=CH]Nle-NH₂ TFA salt (product of Example 1, Step 6, 29 mg, 0.089 mmol) was coupled to α-BOC(ε-Nicotinoyl) Lys-OH (47 mg, 0.13 mmol, prepared by EDC/HOBT solution phase coupling). The product was recovered as an oil. Characteristic NMR Resonances; ¹H NMR 400 MHz (CD₃OD); 8.98 (brd, 1H), 8.68 (brd, 1H), 8.23 (d, 1H, J=8.1 Hz), 7.90 (d, 1H, 8.4 Hz), 7.54 (m, 1H), 5.56 (2H, AB of ABXY, Δδ=23.2 Hz, JAB= 15.5 Hz, JAX=8 Hz, JBY=5.6 Hz), 4.33 (m, 1H), 3.99 (m, 1H), 3.40 (t, 2H, J=7.1 Hz), 2.87 (q, 1H, J=7.5 Hz), 1.42 (s, 9H), 0.897 (t, 3H, J=7 Hz), 0.88 (t, 3H, J=7 Hz).

Step 2

Preparation of TFA (ε-Nicotinoyl)(L)Lys Nvaψ[E, CH=CH]Nle-NH₂

Using the general TFA BOC cleavage as for Example 1, Step 6 above; from the (α-BOC) compound, the deprotected intermediate was obtained in essentially quantitative yield.

Step 3

Preparation of N-(3-CYCLOHEXYLPROPYL)-(L)(ε-NICOTINOYL)Lys Nvaψ[E,CH=CH]Nle-NH₂ TFA SALT General Reductive Alkylation Procedure

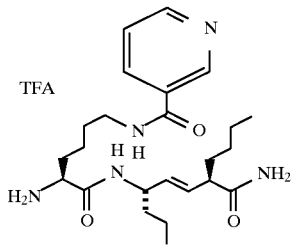

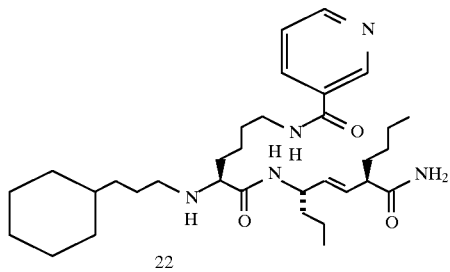

The TFA salt (product of Example 7, Step 3, 1.0 Eq, 0.028 mmol, 15.7 mg) was dissolved in CH₃OH (500 μL). Glacial AcOH (2.0 Eq, 0.056 mmol, 3.2 μL) and iPr₂EtN (1.0 Eq, 0.028 mmol, 4.9 μL) were added, followed by 3-cyclohexylpropionaldehyde (Distilled, 1.0 Eq, 0.028 mmol, 4.3 μL). A 1.0M THF solution of NaCNBH₃ (1.2 Eq, 0.034 mmol, 3.7 μL) was added at RT after brief stirring. Mild gas evolution was noted throughout the reaction. After 2 Hrs. the mixture was acidified with several drops of 2N HCl and stirred ½ Hr. The mixture was diluted with CH₂Cl₂ and satd. aq sodium bicarbonate and extracted 4 times with CH₂Cl₂. The organic phase was dried over Na₂SO₄ and reduced i. vac. The crude product was purified by elution from a Sephadex LH-20-100 column to obtain the title compound. MS ESI 80% AcCN/0.1% Aq TFA 570.3, M+1 for calculated 569.4. Characteristic NMR Resonances; ¹H NMR 400 MHz (CD₃OD); 8.97 (d, 1H, J=1.4 Hz), 8.66 (d, 1H, J=4.9 Hz), 8.23 (m, 1H), 7.53 (dd, 1H, J=4.9, 7.9 Hz), 5.57 (2H, AB of ABXY, Δδ=25.8 Hz, JAB=15.6 Hz, JAX=8.4 Hz, JBY=5.6 Hz), 4.38 (q with fine splitting, 1H, J approx. 7.4 Hz), 3.39 (t, 3H, J=7 Hz), 3.10 (t with fine splitting, 1H, J approx. 7 Hz), 2.88 (q, 1H, J=7.6 Hz), 2.46 (m, 2H), 0.91 (t, 3H, J=7.3 Hz), 0.88 (t, 3H, J=7.2).

EXAMPLE 8

α-(3-CYCLOHEXYLPROPYL)-(L)(ε-NICOTINOYL)Lys Nvaψ[(E)CH=CH]Leu-NH₂ TFA SALT

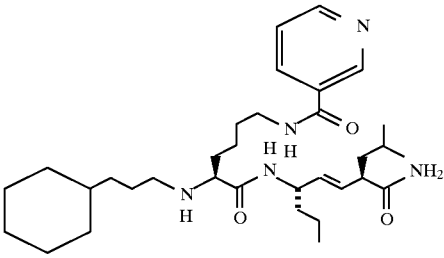

Step 1

Preparation of (α-BOC)(ε-Nicotinoyl)(L)Lys Nvaψ [E,CH=CH] Leu-NH₂

Using the general EDC/HOBT coupling as for Example 4, Step 6 above; from TFA—H—Nvaψ[(E)CH=CH]Leu-NH₂ (product of Example 2, Step 6, 16 mg, 0.049 mmol) and (α-BOC)(ε-Nicotinoyl)Lys-OH (25.8 mg, 0.074 mmol), the desired coupling product was obtained. Characteristic NMR Resonances; ¹H NMR 400 MHz (CD₃OD); 8.97 (d, 1H, J=1.4 Hz), 8.67 (dd, 1H, J=4.9, 1.6 Hz), 8.24 (m, 1H), 7.54 (m, 1H), 5.55 (2H, collapsed AB pattern), 4.31 (m, 1H), 3.99 (m, 1H), 3.40 (t, 2H, J=6.9 Hz), 3.01 (q with fine splitting, 1H), 1.42 (s, 9H), 0.89 (overlapping m's, 9H).

Step 2

Preparation of TFA (ε-Nicotinoyl)(L)Lys Nvaψ[E, CH=CH] Leu-NH₂

Using the general TFA BOC cleavage as for Example 1, Step 6; from the (α-BOC) compound (16.6 mg), the deprotected intermediate was obtained. Characteristic NMR Resonances; ¹H NMR 400 MHz (CD₃OD); 8.97 (brd, 1H), 8.68 (brd, 1H), 8.24 (dt, 1H, J=7.9, 1.9 Hz), 7.54 (dd, 1H, J=4.9, 7.9 Hz), 5.58 (2H, collapsed AB pattern),4.36 (q, 1H, J=6.4 Hz), 3.81 (t, 1H, J=6.5 Hz), 3.42 (t, 2H, J=7.1 Hz), 3.04 (q, 1H, J=7.5 Hz), 1.89 (m, 2H), 1.68 (m, 1H), 0.92 (m's, 6H, overlapping methyl resonances), 0.87 (d, 3H, J=6.2 Hz).

Step 3

Preparation of α-(3-Cyclohexylpropyl)(ε-Nicotinoyl)(L)Lys Nvaψ[E,CH=CH]Leu-NH₂

Using the general reductive alkylation protocol as for Example 7, Step 3 above; from the α-amino compound (14 mg), the cyclohexylpropyl alkylated tetrapeptide mimic (23) was obtained. MS ESI 80% AcCN/0.1% Aq TFA 570.3, M+1 for calculated 569.4. Characteristic NMR Resonances; ¹H NMR 400 MHz (CD₃OD); 8.97 (brd, 1H), 8.67 (d, 1H, J=3.7 Hz), 8.23 (dd, 1H, J=7.9, 1.8 Hz), 7.53 (dd, 1H, J=7.9, 4.9 Hz), 5.58 (2H, collapsed AB pattern),4.4 (q with fine splitting, 1H), 3.41 (overlapping m's 3H), 3.04 (q, 1H, J=7.5 Hz), 2.67 (t, 1H, J=7.7 Hz), 0.925 (t, 3H, J=7.2Hz), 0.90 (d, 3H, J=6.3), 0.87 (d, 3H, J=6.3 Hz).

EXAMPLE 9

α-(3-CYCLOHEXYLPROPYL)-(L)(3-PYRIDYL)
Ala Nvaψ[(E)CH=CH]Leu-NH$_2$ TFA SALT

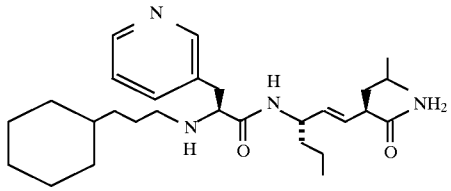

Step 1

Preparation of α-(BOC)(L)(3-Pyridyl)Ala Nvaψ[E, CH=CH]Leu-NH$_2$

Using the general EDC/HOBT coupling as for Example 4, Step 1 above; from TFA—H—Nvaψ[(E)CH=CH]Leu-NH$_2$ (product of Example 2, Step 6, 16 mg, 0.049 mmol) and (α-BOC) (3-Pyridyl)Ala-OH (19.6 mg, 0.074 mmol, prepared by EDC/HOBT solution phase coupling), the desired coupling product was obtained. Characteristic NMR Resonances; $^1$H NMR 400 MHz (CD$_3$OD); 8.4 (m, 2H), 7.74 (dt, 1H, J=7.9, 1.8 Hz), 7.37 (dd, 1H, J=7.9, 5 Hz), 5.48 (2H, collapsed ABXY pattern), 4.29 (m, 2H), 3.06 (2H, AB of ABX, Δδ=96.9 Hz, JAB=14.1 Hz, JAX=5.8 Hz, JBX=9.3 Hz), 2.99 (q, 1H, J=7.4 Hz), 1.42 (s, 9H), 0.91 (overlapping m's, 9H).

Step 2

Preparation of TFA (3-Pyridyl)(L)Lys Nvaψ[E, CH=CH]Leu-NH$_2$

Using the general TFA BOC cleavage as for Example 1, Step 6 above; from the (α-BOC) compound, the deprotected intermediate was obtained. Characteristic NMR Resonances; $^1$H NMR 400 MHz (CD$_3$OD); 8.5 (brd, 1H), 8.45 (brd, 1H), 7.74 (d, 1H, J=7.9 Hz), 7.45 (dd, 1H, J=4.9, 7.6 Hz), 5.58 (2H, AB of ABXY, Δδ=43.4 Hz, JAB=15.7 Hz, JAX=8.5 Hz, JBY=6.4 Hz), 4.3 (q, 1H, J=6.9 Hz), 4.07 (t, 1H, J=7.1 Hz), 3.16 (2H, AB of ABX, Δδ=43 Hz, JAB=14.3 Hz, JAX=6.7 Hz, JBX=7.4 Hz), 0.93 (d, 3H, J=6.4 Hz), 0.91 (t, 3H, J=7.3 Hz), 0.89 (d, 3H, J=6.4 Hz).

Step 3

Preparation of α-(3-Cyclohexylpropyl)(ε-Nicotinoyl)(L)Lys Nvaψ[E,CH=CH]Leu-NH$_2$ Using the general reductive alkylation protocol as for Example 7, Step 3; from the α-amino compound (14 mg), the cyclohexylpropyl alkylated tetrapeptide mimic was obtained. MS ESI 80% AcCN/0.1% Aq TFA 485.2, M+1 for calculated 484.4. Characteristic NMR Resonances; $^1$H NMR 400 MHz (CD$_3$OD); 8.52 (brd, 1H), 8.45 (brd, 1H), 7.73 (d, 1H, J=7.9), 7.46 (m, 1H), 5.31 (2H, AB of ABXY, Δδ=56 Hz, JAB=15.4 Hz, JAX=8.4 Hz, JBY=6.6 Hz), 4.24 (q, 1H, J=7.1), 3.99 (dd, 1H, J=9.5, 5.2 Hz), 3.21 (2H, AB of ABX, Δδ=50 Hz, JAB=13.6 Hz, JAX=4.9 Hz, JBX=9.6 Hz), 2.8–3.05 (overlapping m's, 3H), 0.9 (overlapping methyl resonances, 9H).

EXAMPLE 10

Oral Composition

As a specific embodiment of an oral composition of a compound of this invention, 5 mg of a compound of structural formula I is formulated with sufficient finely divided lactose to provide a total amount of 580 to 590 mg to fill a size 0 hard gelatin capsule.

Biological Assays
Binding and Inhibition Assays

For direct binding assays, optimal concentrations of affinity purified DR1Dw1 (1.25 nM) or DR4Dw4 (10 nM) are incubated with serial dilutions of biotinylated rat myelin basic protein (0) 90–102 in PBS (phosphate buffered saline) containing 0.75% octyl glucoside, pH 6.5, in 96-well polypropylene plates for 16 to 20 h at 37° C. In studies optimizing the assay it was determined that only between 5 to 10% of the DR molecules are capable of binding added peptide. Therefore, the effective concentration of DR1Dw1 and DR4Dw4 was approximately 0.125 and 1.0 nM, respectively. The conditions of the assays are shown to be in ligand excess, because twofold reduction of these class II concentrations does not change the measured ED$_{50}$ values. The DR-peptide complexes (50 μL) are transferred to wells of a 96-well EIA plate precoated with LB3.1, the monoclonal antibody which recognizes the DR alleles of MHC Class II, and blocked with PBS with fetal calf serum (FCS). An additional 50 μL of 50 mM Tris, pH 7.0, containing 0.75% octyl glucoside is added to each well and the mixture incubated overnight at 4° C. Excess peptide is removed by washing with PBS containing 0.05% Tween 20 (Polyoxyethylene sorbitan monolaurate) and 0.01% NaN$_3$. Europium-labeled streptavidin (Wallac Inc.) is added and incubated overnight. After washing, complexes are measured by the addition of Enhance™ buffer, the tradename for 0.1M acetate phthalate buffer, pH 3.2, containing 0.1% Triton X-100, tradename for polyoxyethylene ethers and other surface active compounds of Union Carbide Chemicals and Plastics Co., Inc. (particularly, a non-ionic surfactant for recovery of membrane components under non-denaturing conditions) 15 μM 2-naphthoyltrifluoroacetone, and 50 μM tri-N-octylphosphine oxide, which buffer releases the chelated europium from streptavidin and forms a highly fluorescent micellar solution. The resultant fluorescence is measured using a fluorescent plate reader (e.g., DELPHIA, Wallac, Inc.). The data are analyzed using a four-parameter logistical curve tilt program (e.g., SigmaPlot) that calculates the concentration of biotinylated peptide giving a half-maximal signal (ED$_{50}$).

The ability of LB3.1 to bind DR1Dw1 and DR4Dw4 is shown to be equivalent by measuring the capacity of Ab-coated plates to bind serial dilutions of biotinylated DR molecules. Europium streptavidin is used to measure the number of DR molecules bound as described for the peptide binding assay.

The effects of pH on HLA-DR binding of RMBP 90–102 are explored by performing assays over a range from 4.0 to 9.0. The equivalently low ED$_{50}$ values are observed between pH 5.0 and 6.5, consistent with previous reports. Both lower IC$_{50}$ values and higher percentage occupancy are observed when octyl glucoside was used compared with Tween 20, dodecyl-β-D-maltoside, NP-40, CHAPS, octanoyl-N-methyl-glucamide, and Triton X-100.

The inhibition assay format is identical to the procedure described above with the exception that the unlabeled antagonist is serially diluted and incubated with constant concentrations of biotinylated RMBP 90–102 (0.3 nM for DR1Dw1 or 0.9 nM for DR4Dw4) and the MHC class II proteins. The concentration of unlabeled compound that prevents 50% of the labeled peptide from binding is the IC$_{50}$ value. The concentration of the biotinylated RMBP 90–102 in each assay is experimentally determined to be at least one-sixth of its measured ED$_{50}$ to assure the inhibition was primarily measuring the binding characteristics of the competitor. This was confirmed by demonstrating that a two- or four fold reduction in the biotinylated agonist peptide did not alter the $IC_{50}$ values obtained with unlabeled competitor proving that the receptor concentration was not limiting.

In particular, a protocol for carrying out the inhibition assay is given below.

Preparation of antibody plate

Day 1)

Add 115 μL of 5 μg/mL LB3.1 in 50 mM Tris HCl pH 9.6/azide to each well of a Costar EIA plate. Incubate the plate overnight at 4° C.

Day 2)

Wash the plate 4 times with water/0.05% Tween-20/azide. Add 200 μL of PBS/5% FCS/azide for 1 hour at 4° C. to block the plate. The plate may be held at this point for later use or used immediately.

Flip out the block. It is not necessary to wash the plate. At 50 μL of load buffer (50 mM Tris HCl, pH 8.0 0.75% octylglucoside). Add to this volume 50 μL of the reaction mix from day 2, step 3 below.

Preparation of reaction mixture

Day 2)

(1) Add the following to a polypropylene round bottom 96-well plate such as a Costar #3794:
  (A) Diluent (Ca Mg free PBS adjusted to pH 6.5 with 0.1M $KH_2PO_4$/0.75% octylglucoside/azide)0.81 μL
  (B) Competitor at 16.6 times the final concentration in diluent or diluent alone 0.9 μL
  (C) Biotinylated rat myelin basic protein (BRMBP) 90–102; 1.5 nM for DR1 or 4.5 nM for DR4 (These are 5×stocks of final concentrations of 0.3 nM/DR1 or 0.9 nM/DR4) 30 μL
  (D) 6.25 nM DR1Dw1 or 50 nM DR4Dw4 (these are Drosophila transmembrane DR) (This is a 5×stock of the final concentration of 1.25 or 10 nM.) 30 μL Add the DR last and mix well at this time 150 μL (2) Incubate at 37° C. for 20 min and 5 hours.

(3) Add 50 μL of this reaction mixture to one well of the blocked antibody plate from day 2 above.

(4) Incubate overnight at 4° C. to capture the DR-peptide complexes.

(5) Wash 4× with $H_2O$/0.05% Tween-20/azide (6) Add 125 μL of 100 ng/mL europium streptavidin (Wallac Inc.) in Ca Mg free PBS with 3.5 mg DTPA, 1.6 mL of 30% BSA/500 mL to each well.

(7) Incubate 2 to 4 hours at 4° C.

(8) Wash 4 times.

(9) Add 125 μL of Enhance™ buffer (described above) and incubate at room temperature.

(10) Read the plates.

Representative of $IC_{50}$ values for inhibition of peptide binding to DR1 for compounds of the present invention are shown in the following table:

| Example | $IC_{50}$/nM @ 20 min | $IC_{50}$/nM @ 5 Hrs |
| --- | --- | --- |
| 4 | 37 | 194 |
| 5 | 21 | 142 |
| 6 | 616 | |
| 7 | 409 | 2,280 |
| 8 | 1,052 | 5,600 |
| 9 | 2,525 | 16,650 |

While the invention has been described and illustrated with reference to certain particular embodiments thereof, those skilled in the art will appreciate that various changes, modifications and substitutions can be made therein without departing from the spirit and scope of the invention. For example, effective dosages other than the particular dosages as set forth herein above may be applicable as a consequence of variations in the responsiveness of the mammal being treated for any of the indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of structural formula I:

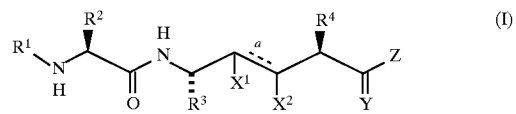

or a pharmaceutically acceptable salt or ester thereof wherein:
  the bond represented by the dotted line "a" is selected from a single bond and a double bond;
  when "a" represents a double bond $X^1$ and $X^2$ are each hydrogen;
  when "a" represents a single bond, $X^1$ and $X^2$ are each $H_2$, or $X^1$ and $X^2$ together are $CH_2$, forming a cyclopropane ring with the "a" bond;
  Z is selected from:
    (a) $NH_2$,
    (b) $NHR^7$,
    (c) OH, and
    (d) $OR^7$;
  Y is selected from:
    (a) O, and
    (b) H,H;
  $R^1$ is

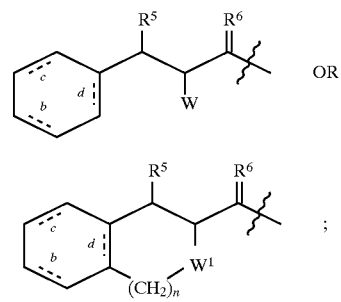

$R^2$ is:
    (a) $C_{1-8}$ alkyl, unsubstituted or substituted with one substituent selected from:
      (1) —$CONHR^8$,
      (2) —$COOR^8$,
      (3) —COOH,
      (4) OH,
      (5) alkoxy,
      (6) —$NHC(O)R^8$,
      (7) pyridyl,
      (8) $NH_2$, and
      (9) $NHR^8$;

$R^3$ is $C_{2-6}$ alkyl, unsubstituted or substituted with one substituent selected from:
(a) $C_{3-8}$cycloalkyl,
(b) aryl,
(c) $CF_3$, and
(d) halogen;
$R^4$ is $C_{2-6}$ alkyl, unsubstituted or substituted with one substituent selected from:
(a) $C_{3-8}$cycloalkyl,
(b) aryl,
(c) $CF_3$, and
(d) halogen;
$R^5$ is selected from:
(a) hydrogen, and
(b) $C_{1-5}$ alkyl;
$R^6$ is selected from:
(a) two hydrogens,
(b) hydrogen and $C_{1-5}$ alkyl, and
(c) =O (carbonyl);
$R^7$ is selected from:
(a) hydrogen, and
(b) $C_{1-5}$ alkyl, unsubstituted or substituted with one substituent selected from:
(1) $C_{3-8}$cycloalkyl,
(2) aryl,
(3) OH,
(4) $NH_2$, and
(5) halogen;
at each occurrence, $R^8$ is independently selected from: $C_{1-3}$ alkyl and aryl;
the bonds represented by the dotted lines "b", "c", and "d" are all double bonds or are all single bonds;
n is selected from zero, 1 and 2;
W is selected from:
(a) hydrogen,
(b) $NH_2$,
(c) $NHR^5$, and
(d) $NHCOR^5$;
$W^1$ is selected from:
(a) O,
(b) NH,
(c) $NR^5$, and
(d) $NCOR^5$;
aryl is selected from:
(a) phenyl,
(b) naphthyl,
(c) indenyl,
(d) thiophenyl,
(e) benzothiophenyl,
(f) furanyl,
(g) benzofuranyl,
(h) pyrollyl,
(i) indolyl, and
(j) pyridyl;
wherein the aryl group may be unsubstituted or substituted with one to three substituents selected from:
(1) $C_{1-4}$ alkyl,
(2) $C_{1-4}$ alkoxy,
(3) halogen, and
(4) hydroxy.
2. The compound according to claim 1 wherein:
"a" is a double bond; and
$X^1$ and $X^2$ are each hydrogen.
3. The compound according to claim 2 wherein:
"b", "c" and "d" each represent single bonds,
$R^1$ is 3-cyclohexyl propyl:

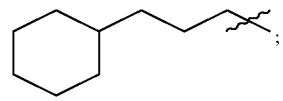

$R^2$ is $C_{1-8}$ alkyl, unsubstituted or substituted with one substituent selected from:
(1) —$CONHR^8$,
(2) —$NHC(O)R^8$,
(3) pyridyl,
(4) $NH_2$, and
(5) $NHR^8$,
$R^3$ and $R^4$ each represent unsubstituted $C_{2-6}$ alkyl; and
at each occurrence, $R^8$ is independently selected from: $C_{1-3}$alkyl, and aryl.
4. The compound according to claim 3 wherein:
$R^3$ is ethyl or propyl and $R^4$ is propyl, butyl or isobutyl.
5. The compound according to claim 1 wherein:
"a" is a single bond and $X^1$ and $X^2$ are each $H_2$.
6. The compound according to claim 5 wherein:
"b", "c" and "d" each represent single bonds,
$R^1$ is 3-cyclohexyl propyl:

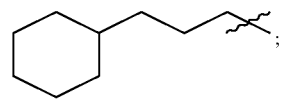

$R^2$ is $C_{1-8}$ alkyl, unsubstituted or substituted with one substituent selected from:
(1) —$CONHR^8$,
(2) —$NHC(O)R^8$,
(3) pyridyl,
(4) $NH_2$, and
(5) $NHR^8$;
$R^3$ and $R^4$ each represent unsubstituted $C_{2-6}$ alkyl; and
at each occurrence, $R^8$ is independently selected from: $C_{1-3}$alkyl, and aryl.
7. The compound according to claim 6 wherein:
$R^3$ is ethyl or propyl and $R^4$ is propyl, butyl or isobutyl.
8. The compound according to claim 1 wherein:
"a" is a single bond and $X^1$ and $X^2$ together are $CH_2$, forming a cyclopropane ring with the "a" bond wherein the substituents on the "a: bond are in the trans configuration.
9. The compound according to claim 8 wherein:
"b", "c" and "d" each represent single bonds;
$R^1$ is 3-cyclohexyl propyl:

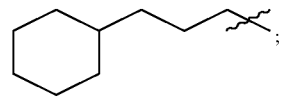

$R^2$ is:
(a) $C_{1-8}$ alkyl, unsubstituted or substituted with one substituent selected from:
(1) —$CONHR^8$,
(2) —$NHC(O)R^8$,
(3) pyridyl,
(4) $NH_2$, and
(5) $NHR^8$;
$R^3$ and $R^4$ each represent unsubstituted $C_{2-6}$ alkyl; and at each occurrence, $R^8$ is independently selected from: $C_{1-3}$alkyl, and aryl.

10. The compound according to claim 9 wherein:
$R^3$ is ethyl or propyl and $R^4$ is propyl, butyl, or isobutyl.

11. The compound according to claim 1 selected from the group consisting of:
EtOCO-Phe Lys Abu ψ[E,CH=CH]Nva-NH$_2$,
EtOCO-Cha Lys Abu ψ[E,CH=CH]Nva-NH$_2$,
EtOCO-Cha Lys Nva ψ[E,CH=CH]Leu-NH$_2$,
EtOCO-Cha Lys Nva ψ[CH2CH2]Leu-NH$_2$,
EtOCO-Cha Lys Nva ψ[E,CH=CH]Nle-NH$_2$,
EtOCO-Cha Orn Nva ψ[E,CH=CH]Nle-NH$_2$,
EtOCO-Cha Arg Nva ψ[E,CH=CH]Nle-NH$_2$,
EtOCO-Cha Lys Nva ψ[trans,cPr]Nle-NH$_2$,
cHx(CH$_2$)$_3$-Lys Nva ψ[E,CH=CH]Nle-NH$_2$,
[3R-(3-cyclohexyl-3-methyl)propyl]-Lys Nva ψ[E,CH=CH]Nle-NH$_2$,
[trans-(1S,2R)-2-cyclohexylcyclopropyl-1-methyl]-Lys Nva ψ[E,CH=CH]Nle-NH$_2$,
[(2R)-(1,2,3,4-Tetrahydronaphthyl)methyl]-Lys Nva ψ[E,CH=CH]Nle-NH$_2$,
[(2S)-(1,2,3,4-Tetrahydronaphthyl)methyl]-Lys Nva ψ[E,CH=CH]Nle-NH$_2$,
[(2R,4aR,8aS)-Octahydrylnaphthylmethyl]-Lys Nva ψ[E,CH=CH]Nle-NH$_2$,
[(2R,4aS,8aR)-Octahydrylnaphthylmethyl]-Lys Nva ψ[E,CH=CH]Nle-NH$_2$,
[(2R,4aS,8aS)-Octahydrylnaphthylmethyl]-Lys Nva ψ[E,CH=CH]Nle-NH$_2$,
[(2R,4aR,8aR)-Octahydrylnaphthylmethyl]-Lys Nva ψ[E,CH=CH]Nle-NH$_2$,
cHx(CH2)3-Lys Nva ψ[E,CH=CH]Nle-OEt,
cHx(CH2)3-Lys Nva ψ[E,CH=CH]Norleucinol,
cHx(CH2)3-(ε-Nic)Lys Nva ψ[E,CH=CH]Nle-NH$_2$, and
cHx(CH2)3-(3-Pyr)Ala Nva ψV[E,CH=CH]Nle-NH$_2$.

12. The compound according to claim 1 selected from the group consisting of:
EtOCO-Phe Lys Abu ψ[E,CH=CH]Nva-NH$_2$,
EtOCO-Cha Lys Abu ψ[E,CH=CH]Nva-NH$_2$,
EtOCO-Cha Lys Nva ψ[E,CH=CH]Leu-NH$_2$,
EtOCO-Cha Lys Nva ψ[CH2CH2]Leu-NH$_2$,
EtOCO-Cha Lys Nva ψ[E,CH=CH]Nle-NH$_2$,
EtOCO-Cha Lys Nva ψ[trans,cPr]Nle-NH$_2$,
cHx(CH2)3-Lys Nva ψ[E,CH=CH]Nle-NH$_2$,
[(2R)-(1,2,3,4-Tetrahydronaphthyl)methyl]-Lys Nva ψ[E,CH=CH]Nle-NH$_2$,
[(2S)-(1,2,3,4-Tetrahydronaphthyl)methyl]-Lys Nva ψ[E,CH=CH]Nle-NH$_2$,
[(2R,4aS,8aR)-Octahydrylnaphthylmethyl]-Lys Nva ψ[E,CH=CH]Nle-NH$_2$,
[(2R,4aR,8aS)-Octahydrylnaphthylmethyl]-Lys Nva ψ[E,CH=CH]Nle-NH$_2$,
cHx(CH2)3-Lys Nva ψ[E,CH=CH]Norleucinol,
cHx(CH2)3-(ε-Nic)Lys Nva ψ[E,CH=CH]Nle-NH$_2$, and
cHx(CH2)3-(3-Pyr)Ala Nva ψ[E,CH=CH]Nle-NH$_2$.

13. The compound according to claim 1 selected from the group consisting of:

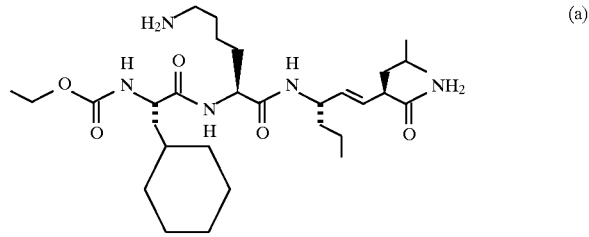

(a) EtOCO—Cha Lys Nva ψ[E,CH=CH]Leu—NH$_2$,

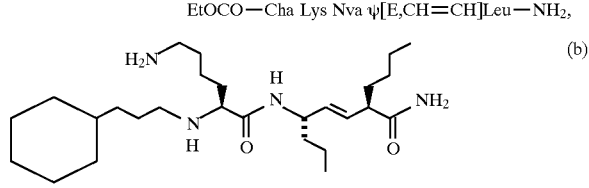

(b) cHx(CH$_2$)$_3$-Lys Nva ψ[E,CH=CH]Nle—NH$_2$,

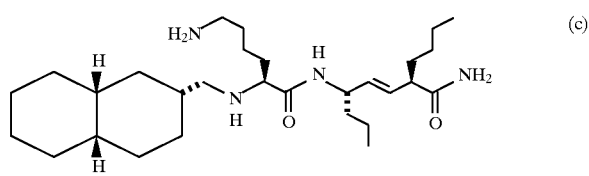

(c) [(2R,4aR,8aS)-Octahydronaphthyl-2-methyl-Lys Nva ψ[E,CH=CH]Leu—NH$_2$,

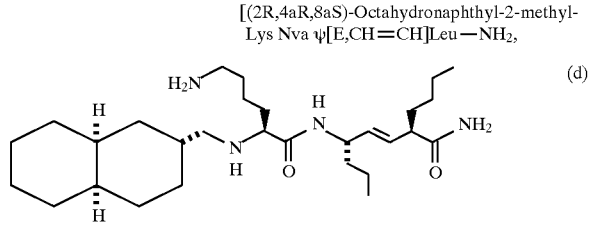

(d) [(2R,4aS,8aR)Octahydronaphthyl-2-methyl]-Lys Nva ψ[E,CH=CH]Leu—NH$_2$, and

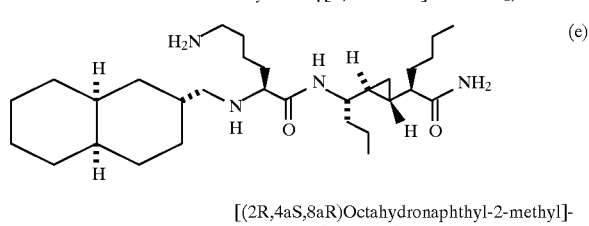

(e) [(2R,4aS,8aR)Octahydronaphthyl-2-methyl]-Lys Nva ψ[trans,cPr]Leu—NH$_2$.

14. A composition comprising a pharmaceutically acceptable carrier and a therapeutically effective amount of a compound of claim 1.

* * * * *